United States Patent [19]
Hayashi et al.

[11] Patent Number: 5,470,956
[45] Date of Patent: Nov. 28, 1995

[54] ANTIBODIES FOR MEVALONIC ACID AND METHODS FOR IMMUNOLOGICAL DETERMINATION OF MEVALONIC ACID BY USING THEM

[75] Inventors: Akio Hayashi; Makoto Hiramatsu; Nobuyuki Hamanaka, all of Osaka, Japan

[73] Assignee: Ono Pharmaceutical Co., Ltd., Osaka, Japan

[21] Appl. No.: 184,178

[22] Filed: Jan. 21, 1994

[30] Foreign Application Priority Data

Jan. 20, 1993 [JP] Japan ................... 5-024747

[51] Int. Cl.$^6$ ............... C07K 16/06; C07K 16/18
[52] U.S. Cl. .................. 530/388.9; 530/389.8; 435/240.27
[58] Field of Search ............ 530/388.9, 389.8; 435/240.27

[56] References Cited

U.S. PATENT DOCUMENTS 4,474,893  10/1984  Reading .................... 436/547
4,722,899   2/1988  Hamaoka et al. ............ 435/172.2

FOREIGN PATENT DOCUMENTS 0459190  12/1991  European Pat. Off.

OTHER PUBLICATIONS

Borrebaeck, Journal of Immunological Methods, vol. 123, pp. 157–165, (1989).
Goodman, Basic & Clinical Immunology, Fedenberg et al. (Eds), LANGE Medical Publications, California, pp. 32–40, (1976).
Robins, Immunology in Plant Sciences, Linskens et al. (Eds), Springer–Verlag, New York, pp. 86–141, (1986).
Bolton et al., "Radioimmunology and Related Methods" Handbook of Experimental Immunology, Weir (Ed.), Blackwell Scientific Publications, pp. 26.1–26.56, (1986).
Goding, Journal of Immunological Methods, vol. 39, pp. 285–308 (1980).
J. Clin. Invest,, 74, 795 (1984), Thomas S. Parker et al., "Plasma Mevalonate as a Measure of Cholesterol Synthesis in Man".
Enzyme Immunoassay, 2nd Edition, Eiji Ishikawa et al. (Eds), published by Igaku Shoin, Japan, pp. 82–126 (1982).

Primary Examiner—Christina Y. Chan
Attorney, Agent, or Firm—Stevens, Davis, Miller & Mosher

[57] ABSTRACT

Polyclonal and monoclonal antibodies are obtained specific to mevalonic acid, having low cross-reactivity with mevalonic acid analogues, such as glutaric acid, 3-methylglutaric acid and 3-hydroxy-3-methylglutaric acid. The antibodies may be used for determination of mevalonic acid providing an immunoassay excellent in sensitivity, specificity and reproducibility.

10 Claims, 3 Drawing Sheets

ANTIBODIES FOR MEVALONIC ACID AND METHODS FOR IMMUNOLOGICAL DETERMINATION OF MEVALONIC ACID BY USING THEM

SUMMARY

The present invention relates to antibodies specific for mevalonic acid and methods for immunological determination of mevalonic acid by using the antibodies thereof.

BACKGROUND

Mevalonic acid is a compound of the following formula:

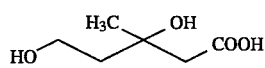

and is an intermediate in cholesterol biosynthesis. Mevalonic acid is biosynthesized from 3-hydroxy-3-methylglutaryl coenzyme A (abbreviated as HMG-CoA hereinafter) by the action of HMG-CoA reductase. Cholesterol in living body is not only biosynthesized according to the above route as well as being taken up from foods.

Until now, the determination of the quantity of biosynthesized cholesterol has been carried out by sterol-balance method. This method is complicated as it comprises subtracting the quantity of cholesterol in foods from the total cholesterol in feces, and therefore, in practice cannot be applied to clinical use.

In 1982, Parker et al. indicated that the quantity of biosynthesized cholesterol is extremely highly correlated to the concentration of mevalonic acid in plasma and revealed that the concentration of mevalonic acid in blood provides an indication of the quantity of biosynthesized cholesterol (J. Clin. Invest., 74, 795 (1984)).

Cholesterol in low density lipoprotein is said to be a contributory factor of arteriosclerosis. Arteriosclerosis can induce myocardial infarction, angina pectoris or cerebral infarction, and can ultimately lead to death.

In the treatment of hypercholesterolemia, it is necessary to judge whether hypercholesterolemia is caused by an excess of cholesterol biosynthesis or by an excessive intake of food high in cholesterol. Appropriate treatment can then be taken (for example, limitation of diet, or administration of HMG-CoA reductase inhibitor and monitoring the quantity of biosynthesized cholesterol after its administration).

Accordingly, it is very important clinically to know the quantity of biosynthesized mevalonic acid in order to assess disorders of lipid metabolism such as hypercholesterolemia.

Related Arts

At present, mass spectrocopy using gas chromatography (GC-MS) and a radioenzymatic methods are known for deter,ruination of mevalonic acid. The mass spectral method has disadvantages in that extraction and derivation of a sample are difficult, the spectrometer used for measurement is expensive, and high level of expertise is required for measurement. The radioenzymatic method carried out by phosphorylating mevalonic acid in a sample using radio-labeled [γ-$^{32}$P]ATP to obtain 5-[$^{32}$P]phosphomevalonic acid, treating with ion-exchange column chromatography and then measuring radioactivity thereof; this method also has practical difficulties in operation.

Accordingly, both methods are inappropriate for mass medical examination in which a large number of samples need to be assayed easily and in a short time.

Means for Solving the Problems

As a result of their energetic investigations for new methods for determination of mevalonic acid, the present inventors have prepared antibodies specific for mevalonic acid which may be used in such a determination.

Antibodies specific for mevalonic acid, regardless of whether they are polyclonal or monoclonal, have never been reported before. Further, new methods for immunological determination of mevalonic acid by using the antibodies thereof have been developed.

CONSTITUTION OF THE INVENTION

The present invention therefore provides antibodies specific for mevalonic acid.

The invention further provides a method of determining mevalonic acid in a sample, which method comprises competitively reacting a labeled antigen and a non-labeled antigen with antibody of the invention, and determining mevalonic acid from the amount of labeled antigen bound or not bound to the antibody, or comprises competitively reacting a immobilized antigen and mevalonic acid in a sample with antibody of the invention, and determining mevalonic acid from the amount of antibody bound or not bound to a immobilize antigen.

The invention also provides antibodies specific to mevalonic acid for use in method of diagnosis.

The invention also provides certain conjugates of protein and mevalonic acid derivatives, useful in obtaining antibodies specific to mevalonic acid.

The invention also provides a kit for determining the amount of mevalonic acid in a sample, said kit containing at least an antibody specific for mevalonic acid and a mevalonic acid derivative or a conjugate of a protein and a mevalonic acid derivative etc.

The present invention includes polyclonal antibodies and monoclonal antibodies.

The present invention includes antibodies having an antigen-binding region other than that of the antibodies obtained in the examples hereinafter described. The antibodies of the present invention can bind specifically to mevalonic acid and cross-reactivities with glutaric acid, 3-methylglutaric acid and 3-hydroxy-3-methylglutaric acid are extremely low.

In antibodies of the present invention, those whose cross-reactivities with glutaric acid, 3-methylglutaric acid and 3-hydroxy-3-methylglutaric acid are less than 1.0%, are preferable. For example, the cross-reactivities of KLH-(12)R, a polyclonal antibody of the present invention, with glutaric acid, 3-methylglutaric acid and 3-hydroxy-3-methylglutaric acid are less than 0.001%, 0.0065% and 0.013%, respectively.

The polyclonal antibodies of the present invention are preferably rabbit polyclonal antibodies, and the monoclonal antibodies of the present invention are preferably mouse monoclonal antibodies. The class and subclass of immunoglobulin are not specifically limited and are preferably IgG and IgM, and more preferably IgG.

The polyclonal antibodies of the present invention may be prepared by:

(1) conjugating a derivative of mevalonic acid with a carrier-protein, (2) immunizing an appropriate animal for immunization by using the derivative of mevalonic acid-protein conjugate as an antigen, and (3) collecting a serum fraction from an immunized animal, to obtain a desired antibody fraction.

Each steps are explained in detail as follows.

Derivatives of a mevalonic acid in step (1) mean compounds introducing directly or indirectly a reactive functional group into a carbon atom at the second, fourth or fifth position of mevalonic acid, into a hydroxy group substituted at the third or fifth position thereof, or into a methyl group substituted at the third position thereof, or compounds introducing directly or indirectly a reactive functional group instead of a methyl or hydroxy group substituted at the third position thereof. Preferably, they are compounds introducing directly or indirectly a reactive functional group into a hydroxy or functional group into a methyl group substituted at the third position thereof. When a free hydroxy group not binding with a reactive functional group, exists in the said derivatives, it may form an intramolecular lactone with a carboxy group at the first position. The reactive functional groups are not specifically limited if the groups can bind directly or indirectly mevalonic acid with carrier-protein. Examples of those groups are a carboxyl (—COOH), hydroxyl (—OH), formyl (—CHO), amino (—$NH_2$), azido (—$N_3$), mercapto (—SH), sulfonyl (—$SO_3H$) group, etc., and preferably a carboxy group.

Examples of a proper carrier-protein are natural proteins such as albumin, globulin, thyroglobulin, hemocyanin, edestin, etc., and synthesized polypeptides such as polylysine, and preferably albumin and hemocyanin. The reactions for conjugating a derivative of mevalonic acid with a carrier-protein are known well, and, for example, are described in "Enzyme Immunoassay", 2nd Edition (1982), edited by Eiji Ishikawa et al., published by Igaku Shoin, pp82 in detail. That is, it may be carried out in an appropriate solvent (e.g. phosphate buffer solution), by using carbodiimide method, acid anhydride method, maleimide method, preferable method by using as a condensing agent, dicyclohexylcarbodiimide or 1-ethyl-3-(3-dimethylaminopropyl)carbodiimide when a derivative of mevalonic acid as hapten can conjugate directly to a carrier-protein, or by using a spacer known in the art, e.g., 1,5-difluoro-2,4-dinitrobenzene when a derivative of mevalonic acid can not conjugate directly to a carrier-protein. After reaction, the objects may be isolated and purified by column chromatography.

The derivatives of mevalonic acid and a conjugate of a derivative of mevalonic acid with a spacer, may be easily prepared according to methods known per se. Representative schemes for the preparation are depicted in the following Scheme I, II, III, IV, V, VI, VII and VIII.

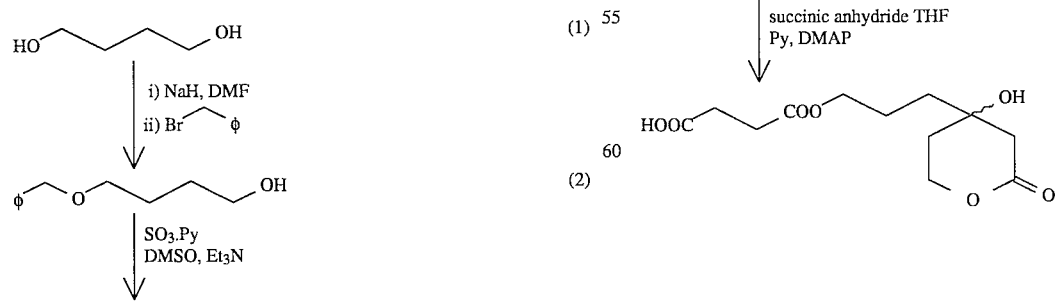

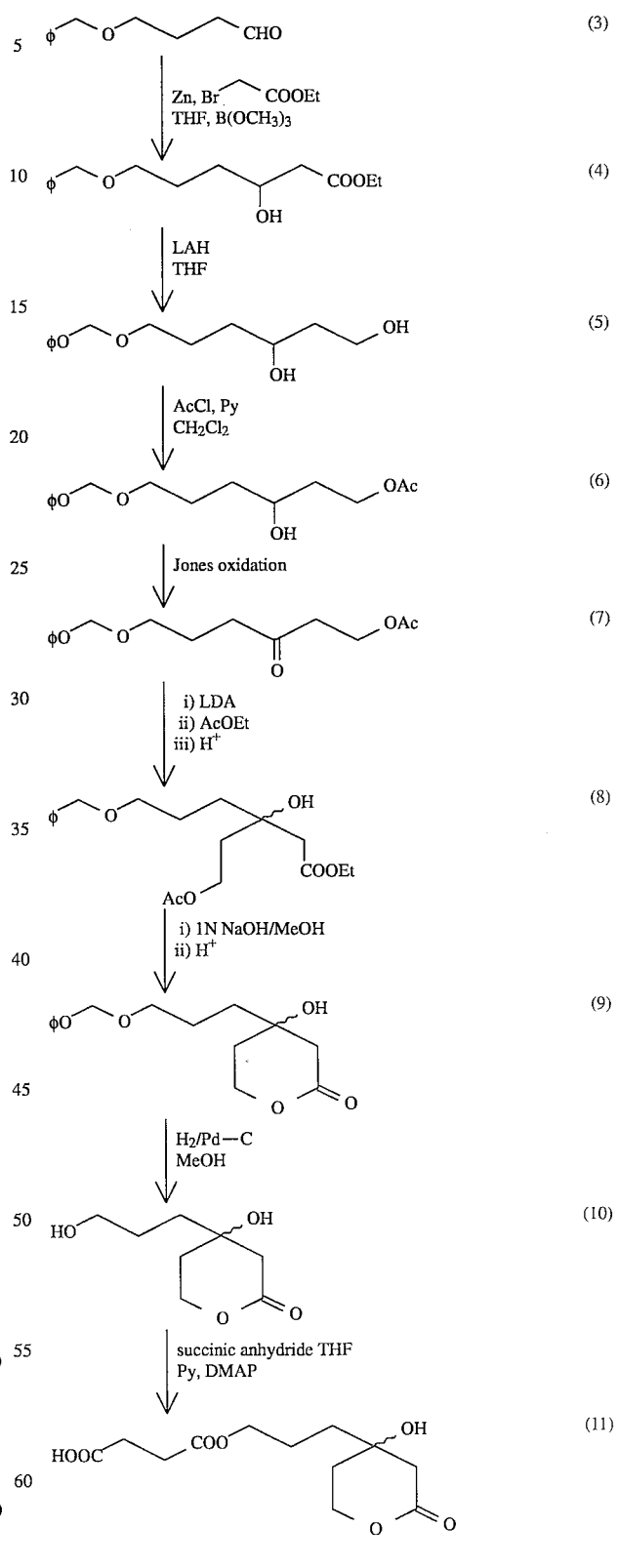

-continued
Scheme I
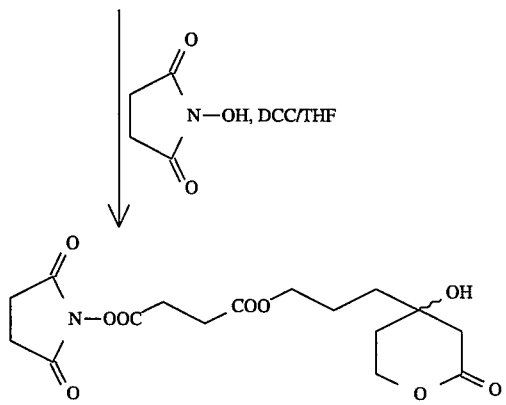
(12)
Scheme II
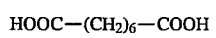
(13)
i) NaH, DMF
ii) Br—CH₂—φ
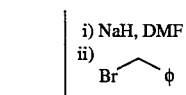
(14)
SOCl₂
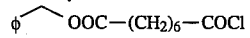
(15)
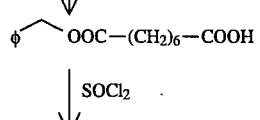
(10)
Py, THF
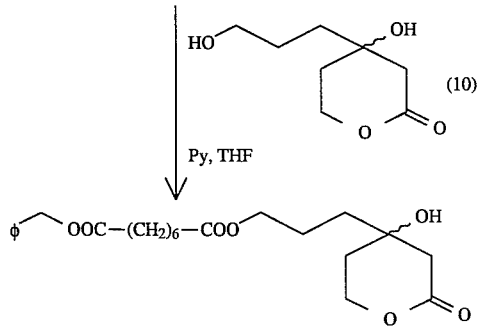
(16)
H₂/Pd—C
MeOH
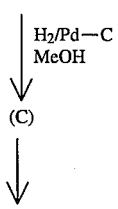
(C)
-continued
Scheme II
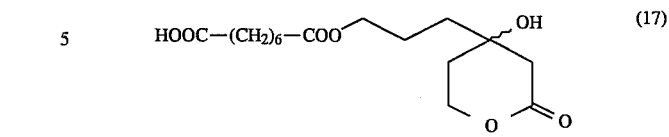
(17)
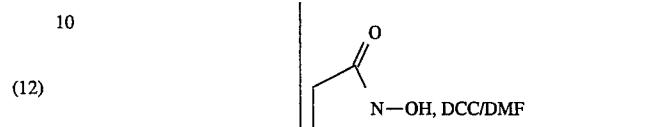
N—OH, DCC/DMF
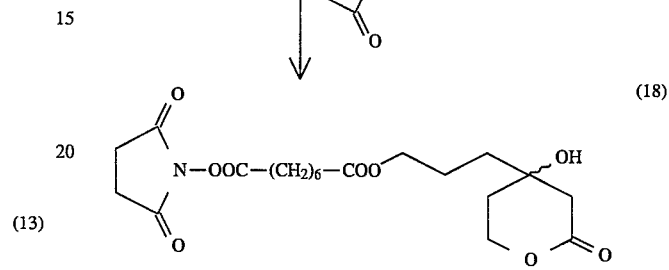
(18)
Scheme III
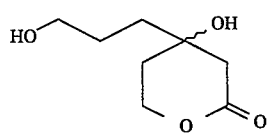
(10)
(ICH₂CO)₂O
THF, DMAP
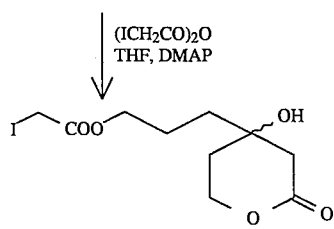
(19)
Scheme IV
HO—(CH₂)₁₂—OH (20)
i) NaH, DMF
ii) Br—CH₂—φH
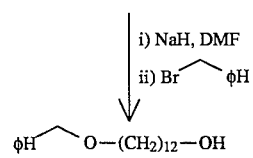
φH—CH₂—O—(CH₂)₁₂—OH (21)
SO₃·Py
DMSO, Et₃N
φH—CH₂—O—(CH₂)₁₁—CHO (22)
Zn, Br—CH₂—COOEt
THF, B(OCH₃)₃
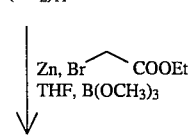

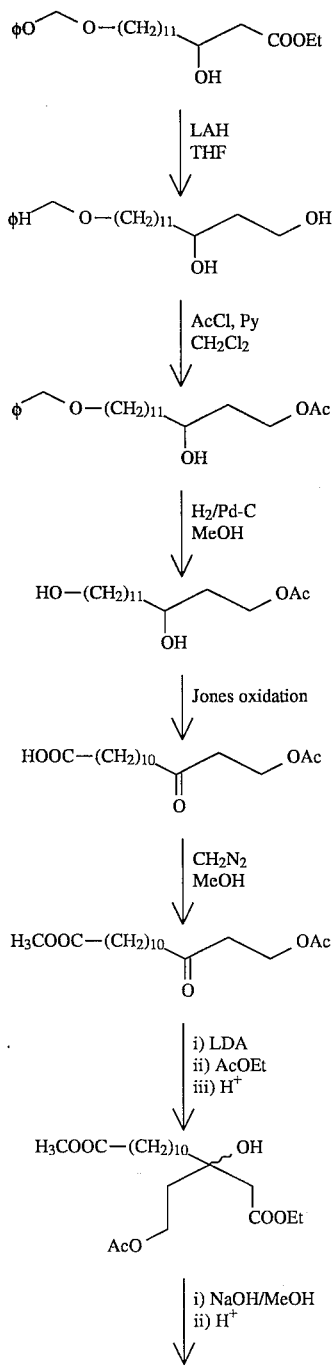
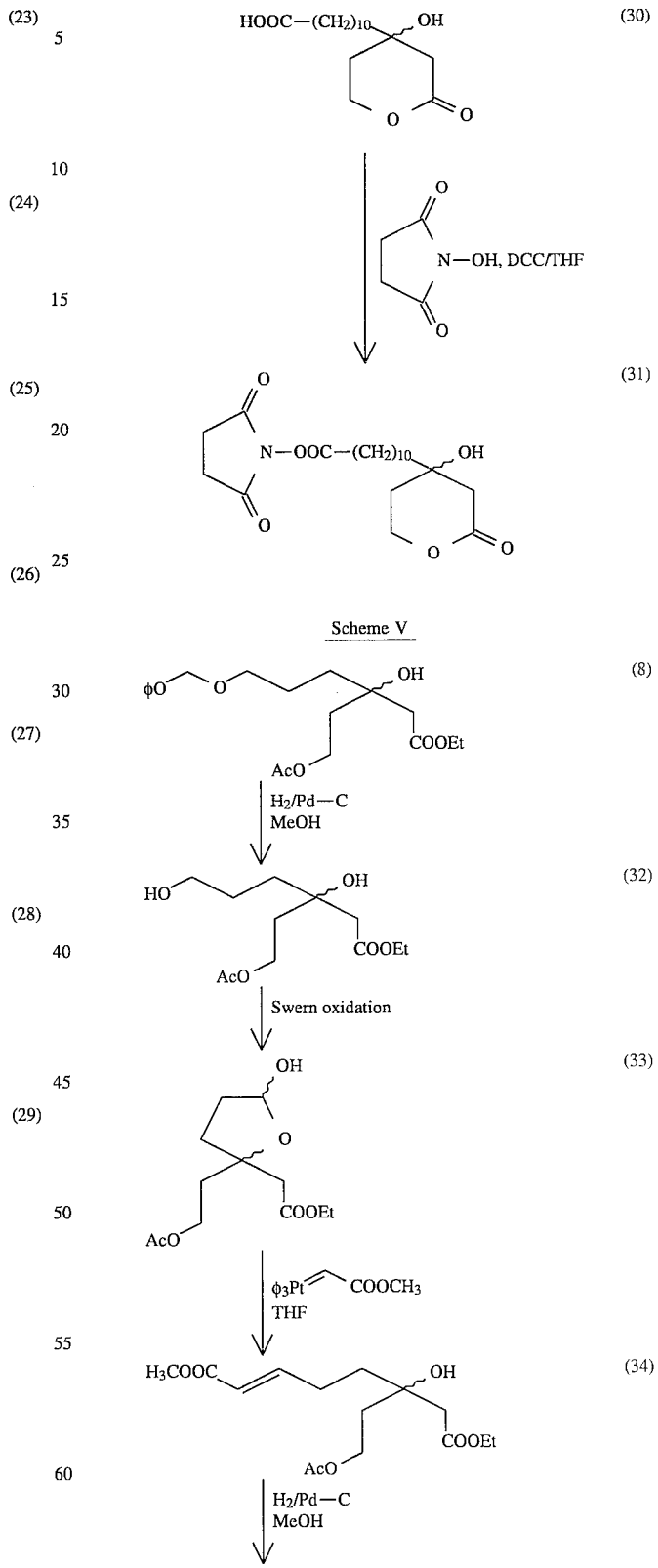

-continued
Scheme V
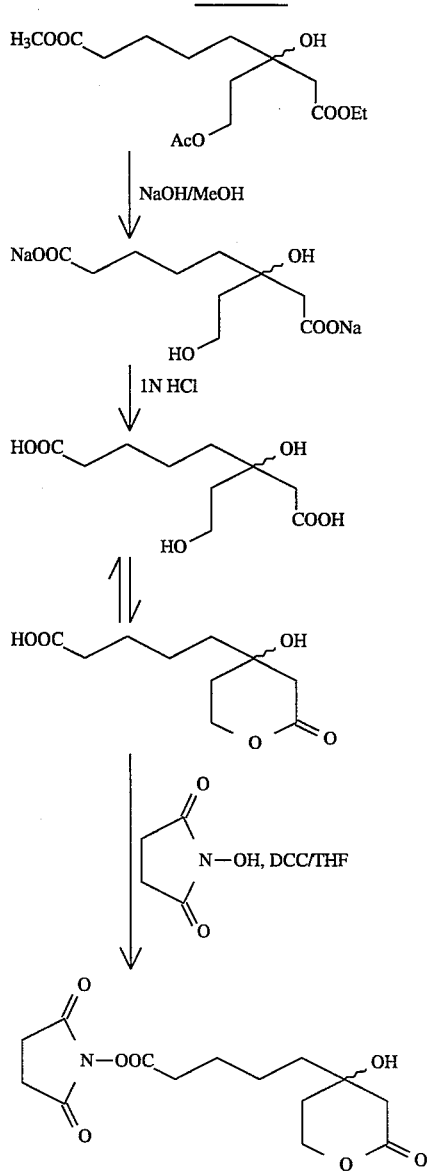
Scheme VI-(1)
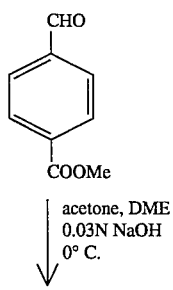
acetone, DME
0.03N NaOH
0° C.
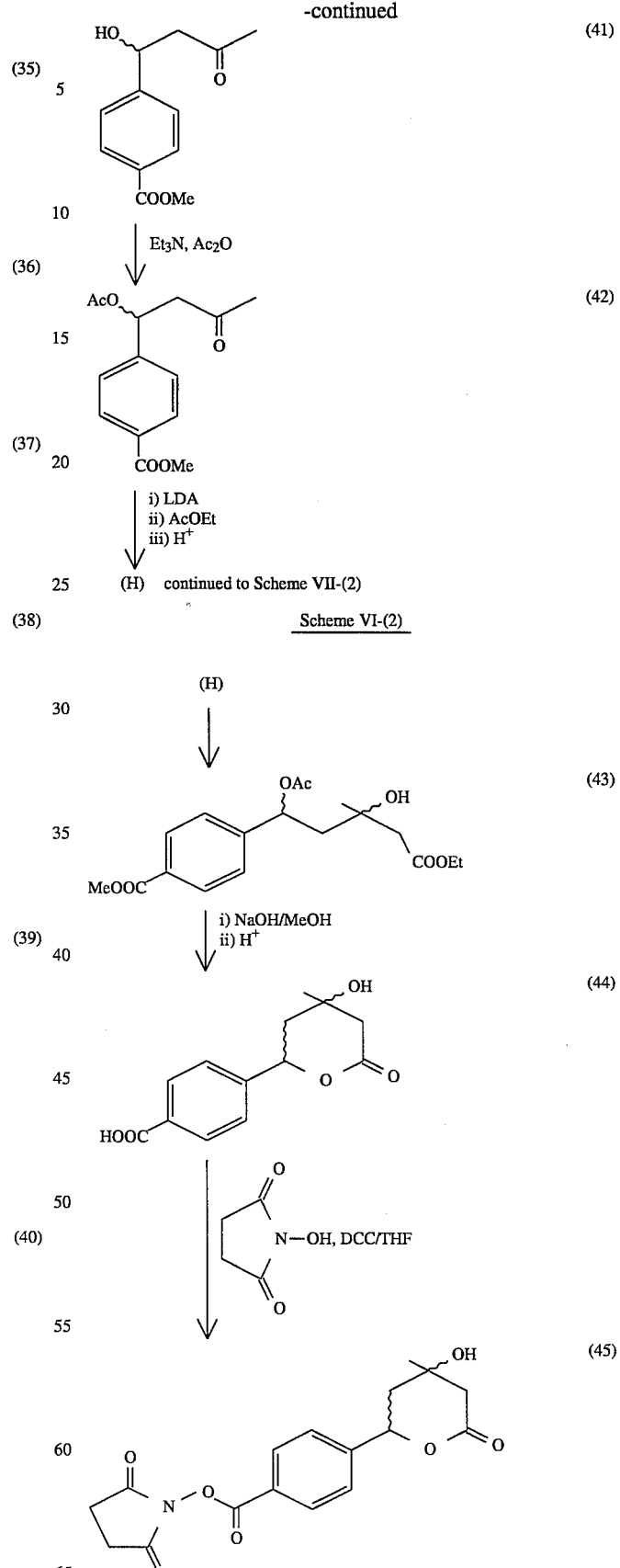
Scheme VI-(2)

Scheme VII-(1)
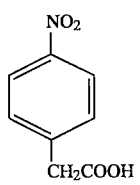
↓ EtI, K₂CO₃, DMF
   70° C.
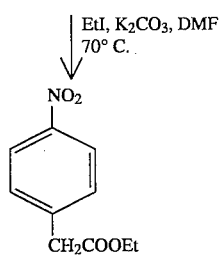
↓ H₂/Pd—C, MeOH
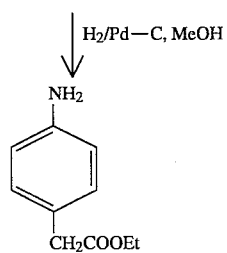
(I) continued to Scheme VII-(2)
Scheme VII-(2)
(I)
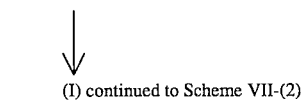, DMAP, 90° C.
↓
(46)
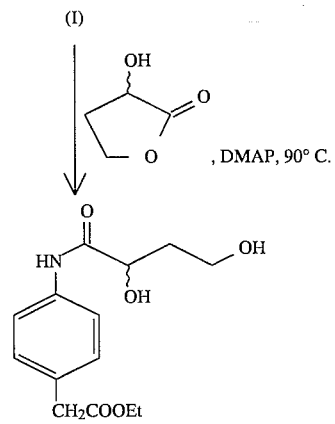
↓ AcCl, Py,
   CH₂Cl₂
-continued
(49)
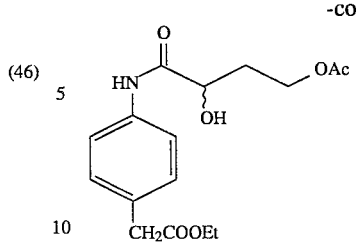
↓ Jones oxidation
(47)
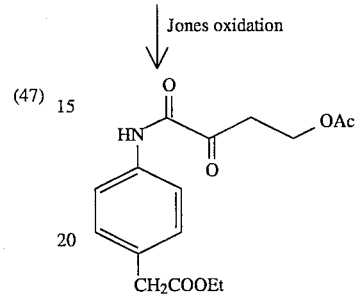
(J) continued to Scheme VII-(3)
Scheme VII-(3)
(J)
↓ i) LDA
  ii) AcOEt
  iii) H⁺
(50)
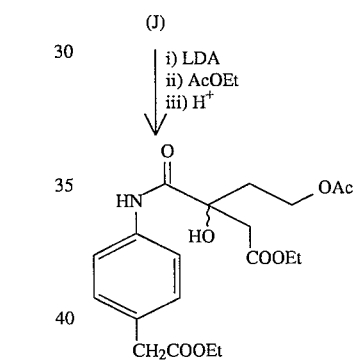
↓ i) NaOH/MeOH
  ii) H⁺
(48)
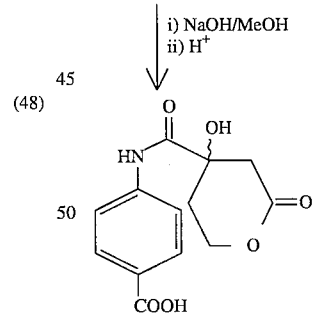
↓ 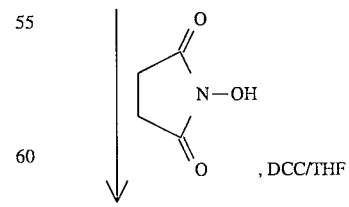, DCC/THF -continued

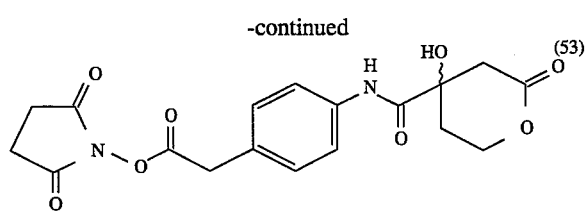

Scheme VIII-(1)

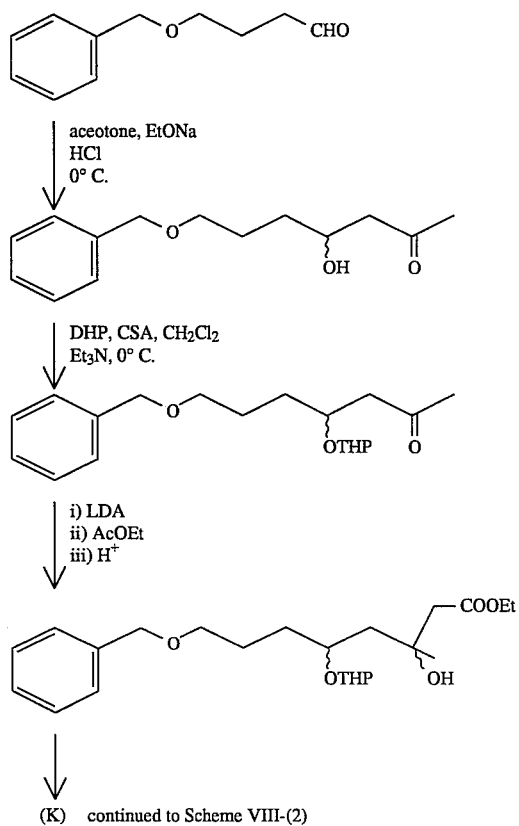

(K) continued to Scheme VIII-(2)

Scheme VIII-(2)

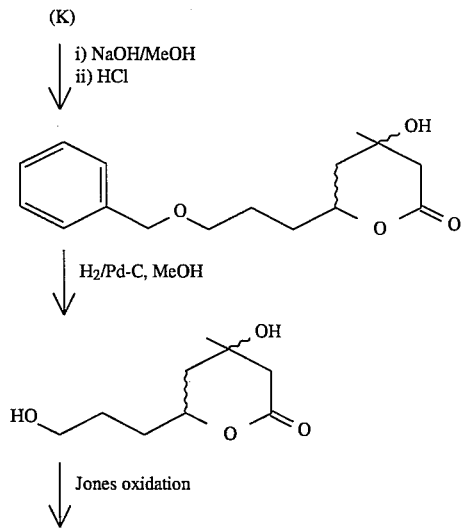

-continued

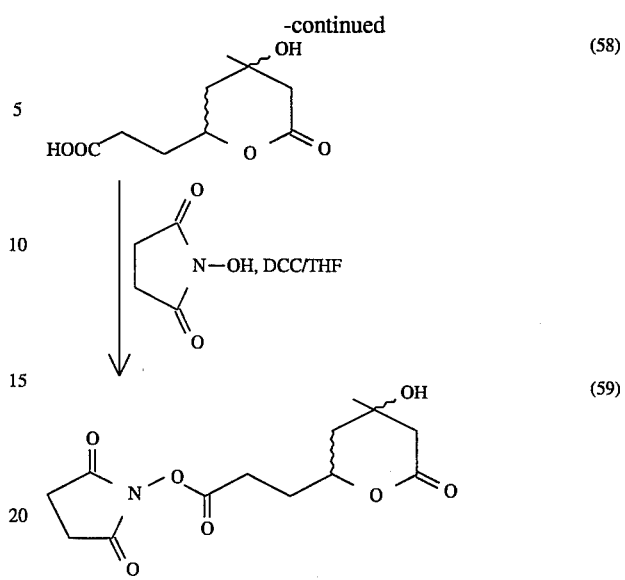

In the schemes hereinbefore described, abbreviations means the following groups and compounds.

φ: phenyl group,
Et: ethyl group,
Ac: acetyl group,
DMF: dimethylformamide,
Py: pyridine,
DMSO: dimethyl formamide,
THF: tetrahydrofuran,
LAH: lithium aluminum hydride,
LDA: lithium diisopropylamide,
AcOEt: ethyl acetate,
MeOH: methanol,
Pd-C: palladium on carbon,
DMAP: 4-dimethylaminopyridine,
DCC: dicyclohexylcarbodiimide,
DME: dimethoxy ethane,
DHP: dihydropyrane, and
CSA: camphorsulfonic acid.

In step (2) for immunization, a form of antigens for immunization are not specifically limited, and it is commonly that a antigen for immunization is administered with a regular adjuvant. An administration may be carried out by intravenously, intradermaly, subcutaneously or intraperitoneally administration. More particularly, when immunizing first, a conjugate of a derivative of mevalonic acid, obtained in (1), and a carrier-protein, may be dissolved into phosphate buffer solution including physiological salt (abbreviated as PBS hereinafter) and then emulsified with complete Freund's adjuvant (abbreviated as FCA hereinafter) at the ratio of 1:1. The emulsion thus obtained, may be subcutaneously administered to animals for immunization. Furthermore, PBS containing a conjugate of a derivative of mevalonic acid and a carrier-protein, may be emulsified with incomplete Freund's adjuvant (abbreviated as FICA hereinafter) at the ratio of 1:1. After the first immunization, the emulsion thus obtained, may be subcutaneously administered to the animals several times at two or three weeks' intervals. The animals for immunization are not specifically limited if the animal is known to produce a polyclonal antibody. Examples of the animals are rabbits, guinea pigs, rats, asses, sheep, goats, fowls, etc. and preferably rabbits, and more preferably New Zealand white rabbits are used. The number of immunization are not specifically limited and it is desired that immunization is carried out until the sufficient titer of antibody is obtained. The doses of the antigen are not specifically limited and for example, 1 to 2 mg (as carrier-protein) may be administered to rabbits.

Step (3) may be carried out by collecting serum of the animal, and isolating and purifying by affinity chromatography, etc.

Furthermore, the monoclonal antibodies of the present invention may be prepared by:

(1) conjugating a derivative of mevalonic acid with a carrier-protein, (2) immunizing an appropriate animal with the derivative of mevalonic acid-protein conjugate as an antigen, (3) fusing spleen cells of immunizing animals and myeloma cells derived from animals whose stain is the same as that of immunized ones, (4) screening cells producing a monoclonal antibody for mevalonic acid, from hybridomas obtained above, (5) cloning a hybridoma producing a desired antibody, (6) multiplying the cloned hybridoma which produces a desired antibody, and (7) isolating and purifying the produced antibody.

Each steps are explained in detail as follows

Step (1) may be carried out by the same procedure as described in step (1) in methods for the preparation of polyclonal antibodies of the present invention.

Step (2) may be also be carried out by the same procedure as described in step (2) in methods for the preparation of polyclonal antibodies of the present invention, but it is preferable that a conjugate of a derivative of mevalonic acid and a carrier-protein should be intraperitoneally administered to animals for immunization when monoclonal antibodies is prepared. The animals for immunization are not specifically limited if the animal is generally known to use for preparing a monoclonal antibody. Examples of the animals are mice, rats, etc. and preferably mice, and more preferably BALB/c is used. The sufficient doses of the antigen are, for example, 100 to 200 μg (as carrier-protein) per time in the case of mice.

Cell-fusion is Step (3) may be carried out by excising a spleen cell of the immunizing animal which has the sufficient titer of antibody, preparing a suspension of the spleen cell according to known methods, and then adding polyethylene glycol (preferably PEG 4000) at 37° C. to a mixture of the obtained spleen cell and myeloma cells derived from animals whose stain is the same as that of immunized ones. Several kinds of mice myeloma cells are known. For example, they are P3X63Ag8, P3/NS1/1-Ag4-1, SP-2/0-Ag-14, etc, and are easily available. HGPRT (hypoxanthine guanine phosphoribosyl transferase) -defective cell lines which can not survive in HAT medium (the medium containing hypoxanthine, aminopterin and thymidine), is useful as myeloma cells. Furthermore, it is preferable that myeloma cells themselves do not secrete an antibody. SP-2/0-Ag-14 may be preferably used.

The mixture of cell-fusion thus obtained may be distributed into 96 micro-well plates with low density of cells and incubated in a HAT medium. After the incubation for one to two weeks, unfused myeloma cells, hybridomas of a comrade in myeloma cells, unfused spleen cells and hybridomas of a comrade in spleen cells can not survive due to the lack of vital conditions. Hybridomas of spleen cells and myeloma cells can only survive and are multiplied.

The screening in (4) may be carried out by reacting an incubation supernatant of hybridomas with labeled mevalonic acid, separating an antibody fraction and determining; the quantity of the label in the antibody fraction or by reacting an incubation supernatant of hybridomas with an antigen coated solid phase and determining the antibody specifically bound to the antigen in supernatant by using the labeled second antibody, to judge whether the hybridoma produces an antibody for mevalonic acid or not.

Step (5) may be carried out by cloning a hybridoma producing a desired antibody according to the soft agar culture method (see Monoclonal Antibodies, pp 372 (1980)). The limited dilution method may also used.

Step (6) may be carried out by culturing the cloned hybridoma in a usual medium and isolating and purifying from an incubation supernatant. It may be also carried out by intraperitoneally administering a hybridoma to mice, multiplying and isolation and purifying from ascites in order to efficiently obtain a large amount of antibody.

Step (7) may be carried out by the purification with usual methods, e.g., salting-out, ion-exchange chromatography, gel filtration, hydrophobic chromatography, affinity chromatography, etc. More efficiently, affinity chromatography with using protein A-cepharose CL-4B (prepared by Pharmacia Co.) may be used.

The antibodies of the present invention are specific for mevalonic acid, and therefore, may be used in the purification and the concentration of mevalonic acid, e.g. affinity chromatography, etc.

The antibodies of the present invention are also usable, in accordance with the invention for immunological determination of mevalonic acid.

Immunological determination may generally be performed by competitive method and non-competitive method. A competitive method is preferably used for immunological determination of a substance having low molecular weight, such as mevalonic acid. Generally, the competitive method may be carried out by competitively reacting a known amount of labeled antigen and a non-labeled antigen (from a sample) with antibody, and then determining the quantity of labeled antigen binding (or not binding) with the antibody by using an appropriate method.

The quantity of labeled antigen bound to antibody may be determined without separation of antigens binding to antibodies from antigens not binding with antibodies (homogenous methods), or determined after separating antigens binding with antibodies (abbreviated as "Bound" or "B")from antigens not binding with antibodies (abbreviated as "Free" or "F") (the separation is referred to "B/F separation" and this method for determination is referred to as a heterogeneous method).

In case of homogeneous competitive immunoassay of low molecule weight species such as mevalonic acid, methods may be used which measure the degree of inhibition of aggregation of labeled antigens and antibodies by non-labeled antigens. Generally, labeled antigens include compounds which are composed of more than two antigens which aggregate to a particle coated by antibodies, and antigens bound to a particle to which antibodies will aggregate.

Methods of homogeneous competitive immunoassay may measure a characteristic change of labeled antigens caused by binding to antibodies, for example, enzymatic activation or inactivation, optimal change (absorbance, fluorescence, luminescence), or electrical change. Other methods which may be used in accordance with the invention measure competition degree by assessing mobility of the labeled antigens which is developed after the labeled antigens and non-labeled antigens are spotted on the antibodies coated solid phase such as filter paper.

In heterogeneous immunoassay, a radio-labeled or enzyme-labeled derivative of mevalonic acid (which cross-reacts with anti-mevalonic acid antibodies) is used as labeled antigen. The radio-isotopes which are commonly used in the immunoassay are $^{3}H$, $^{14}C$, $^{32}P$, and $^{125}I$. The enzyme-labels which can be used include those commonly used for immunoassay, for example peroxidase, β-D-galactosidase, alkaline phosphatase, glucose oxidase, glucose-6-phosphate dehydrogenase, acetyl cholinesterase, and alcohol dehydrogenase.

The methods of B/F separation are not limited specially. In case of using radio-labeled antigens, precipitation by polyethylene glycol, adsorption by active carbon, solid phase antibody methods, and double antibody methods are usable. In case of enzyme-labeled antigens, solid phase antibody methods and double antibody method are usable.

Solid phase antibody method is as follows.

(1) Add the sample solution containing mevalonic acid and the labeled antigens solution to anti-mevalonic acid antibody (the first antibody) coated solid phase for competitive reaction.

(2) After immunoreaction, the content is discarded by decantation, and the amount of mevalonic acid concentration in sample is estimated by measuring the signal of label which is binding to solid phase.

This monoclonal antibody of the present invention is used as the first antibody. The solid phase and the immobilizing method are known commonly (Ichiro Chibata, Koteika Kouso. 1975, Koudansha). For example, polystyrene plate, polystyrene tube, polystyrene bead, nylon bead, glass. bead, protein A agarose bead, and protein G agarose bead are used as solid phase. Physiological adsorption and covalent binding are used for immobilizing. As the label of antigens, for instance, the radio-labeled antigens and the enzyme-labeled antigens which are described before are used.

It is preferable to react the first antibody with sample or labeled antigens at 4° C. for 10 hours.

The measurement of labeled antigens described in (2) is carried out by known method. For example, in the case of peroxidase labeled antigens, 3,3',5,5'-tetramethylbenzidine is used as substrate and is reacted with $H_2O_2$, and then absorbance of reaction product is measured. In this case 3-(p-hydroxyphenyl)propionic acid, o-phenylendiamine, and luminol can be also used as substrate: If another enzyme is used, the assay is carried out with appropriate substrate.

There are two types of double antibody methods. Methods in which the first antibody is reacted with the second antibody in the liquid phase, and double antibody solid phase methods. Double antibody solid phase methods are especially favorable because B/F separation is facilitated by immobilization of the second antibody.

Double antibody solid phase method is as follows.

(1) Immobilize the second antibody against anti-mevalonic acid antibody to solid phase (e.g.; Anti-mouse IgG antibody is used as the second antibody when anti-mevalonic acid antibody is mouse IgG.).

(2) The sample containing mevalonic acid, labeled antigens, and anti mevalonic acid antibody (the first antibody) are added thereto, and the mixture is reacted.

(3) Measure the signal of labeled antigens.

In case of using anti-mouse antibody as the second antibody, both monoclonal and polyclonal antibody can be used, and animal from which the second antibody is derived is not limited especially.

The polyclonal antibody against mouse IgG can be prepared by immunizing mouse serum or mouse g-globulin to the animal of other species (e.g.; rat, guinea pig, rabbit, goat) with commonly known method (rinshyo kensa, 26(7), 777(1982)), otherwise some polyclonal antibodies are commercially available.

Solid phase, immobilization, labeled antibody, the first antibody, measurement of label, reaction temperature and time can be selected properly in accordance with solid phase antibody method.

Alternatively a solid phase antibody method may comprise measurement of the amount of a label conjugated to the first antibody, or to a second antibody which is bound to the first antibody, after competitive reaction of the first antibody with immobilized antigen and mevalonic acid in a sample solution.

Non-competitive immunoassay methods may also be used where the antibody conjugated t:o label shows measurable change on binding to antigens. For example, a moiety, such as luminol, which can produce electrochemical luminescence, may be used as a label attached to an antibody which is immobilized on electrode. Electrochemical luminescence in such a case is diminished when the antigen bind to the labeled antibody.

In the assay of present invention, body fluids such as blood, urine and the like, are generally used as sample.

The Effect of the Present Invention

The antibodies of the present invention thus recognize mevalonic acid specifically and preferably have extremely low cross-reactivity with other similar compounds.

They may be used to establish highly sensitive, specific and reproducible immunoassay for mevalonic acid. This assay of present invention is much easier to perform than conventional methods for determining mevalonic acid using GC-MS or radioenzymatic methods.

EXAMPLES

The following reference examples and examples illustrate, but not limit, the present invention.

In the example, "TLC", "MS", "IR" and "NMR" means "thin layer chromatography", "mass spectrum", "infrared spectrum" and "nuclear magnetic resonance spectrum", respectively.

The solvents in parentheses show the developing or eluting solvents and the ratios of the solvents used are by volume in chromatographic separations.

Example 1: Preparation of the conjugated compound of mevalonic acid derivatives and a spacer (a) Succinimide 3-(4-hydroxy-2-oxotetrahydropyran-4-yl-)propyl succinate (1) To a suspension of 63% sodium hydride (4.68 g) in DMF (60 ml) was added slowly dropwise a solution of 1,4-butandiol (11.0 g) in DMF (10 ml) at 4° C., after the mixture was warmed up to room temperature, and stirred for 30 min. at room temperature. The mixture was added slowly dropwise 13 ml of benzylbromide with cooling at 4° C. The mixture was warmed up to room temperature, and stirred for 22 hour at 70° C. The reaction mixture was extracted with ethyl acetate, and the residue was purified by silica gel column chromatography (hexane:ethyl acetate=8:2) to give the compound (2) (12.8 g) having the following physical data.

TLC: Rf 0.21 (hexane:ethyl acetate=6:4).

(2) To a solution of the compound (2) (4.2 g) in DMSO (20 ml) and triethylamine (22 ml) was added piece by piece a small amount of sulfur trioxide pyridine complex (14.2 g)

with vigorously stirring. The mixture was stirred for 20 min. at room temperature. After the reaction mixture was extracted with diethylether, and purified by silica gel column chromatography (hexane:ethyl acetate=9:1) to give the compound (3) (3.18 g) having the following physical data.

TLC: Rf 0.19 (hexane:ethyl acetate=9:1). (3) To a solution of trimethyl borate (3.42 ml) in THF (52 ml) were added successively zinc (4.02 g) and slowly dropwise ethyl bromoacetate (3.42 ml) at 4° C. After the mixture was stirred for 10 min., and the compound (3) (2.67 g) added thereto. The reaction mixture was stirred for 10 min. The mixture was extracted with ethyl acetate, and was purified by silica gel column chromatography (hexane:ethyl acetate=8:2) to give the compound (4) (3.66 g) having the following physical data.

TLC: Rf 0.52 (hexane:ethyl acetate=6:4).

(4) To a suspension of lithium aluminum hydride (700 mg) in THF (25 ml) was added slowly dropwise a solution of the compound (4) (3.26 g) in THF (5 ml) at room temperature. After the reaction completed, the mixture was quenched by addition of 2N hydrochloric acid, and stirred for 10 min. After the mixture was filtrated through Celite, the filtrate was extracted with ethyl acetate. The extract was concentrated under reduced pressure to give the compound (5) (2.66 g) having the following physical data.

TLC: Rf 0.15 (hexane:ethyl acetate=4:6).

(5) To a solution of the compound (5) (1.657 g) in dichloromethane (25 ml) was added successively pyridine (3 ml), and slowly dropwise acetyl chloride (750 pl) at 4° C. The mixture was stirred for 1.5 hour and diluted with water, and then extracted with ethyl acetate. The crude product was purified by silica gel column chromatography (hexane:ethyl acetate=7:3) to give the compound (6) (1.601 g) having the following physical data.

TLC: Rf 0.30 (hexane:ethyl acetate=6:4).

(6) To a solution of the compound (6) (1.60 g) in acetone (15 ml) was dropped Jones reagent (3 ml) at 4° C. After the reaction mixture was stirred for 10 min., isopropanol (1.5 ml) was added thereto. After stirred for 10 min. at room temperature, the reaction mixture was extracted with ethyl acetate to give the compound (7) (1.48 g) having the following physical data.

TLC: Rf 0.46 (hexane:ethyl acetate=6:4).

(7) To a solution of diisopropylamine (223 µl) in diethylether (2 ml) was added slowly dropwise 1.56M n-butyllithium in hexane solution (971 µl) at −20° C., and then the mixture was stirred for 1 hour. Ethyl acetate (150 µl) was added slowly dropwise thereto at −78° C., and then the mixture was stirred for 30 min. A solution of the compound (7) (200 mg) in diethylether (150 µl) was added thereto. The reaction mixture was stirred for 30 min. The mixture was diluted with a saturated aqueous solution of ammonium chloride, and extracted with ethyl acetate. The residue was purified by silica gel column chromatography (hexane:ethyl acetate=8:2) to give the compound (8) (247 mg) having the following physical data.

TLC: Rf 0.48 (hexane:ethyl acetate=6:4).

(8) To a solution of the compound (8) (30 mg) in methanol (2 ml) was added 1N aqueous solution of sodium hydroxide (213 µl). The reaction mixture was stirred for four hours at room temperature. The mixture was quenched by addition of 1N hydrochloric acid, and then extracted with ethyl acetate. The residue was purified by silica gel column chromatography (hexane:ethyl acetate=6:4) to give the compound (9) (22 mg) having the following physical data.

TLC: Rf 0.28 (hexane:ethyl acetate=4:6).

(9) To a solution of the compound (9) (22 mg) in methanol (2 ml) was added 10% palladium-carbon (20 mg). The mixture was stirred for 1.5 hours at room temperature under an atmosphere of hydrogen. The catalyst was filtered off and the solution was evaporated to give the compound (10) (14 mg) having the following physical data.

TLC: Rf 0.15 (ethyl acetate).

(10) To a solution of the compound (10) (22 mg) and succinic anhydride (80 mg) in THF (2 ml) were added successively pyridine (32 µl) and 4-dimethylaminopyridine (5 mg). The mixture was stirred for 1.5 days at room temperature. The reaction mixture was concentrated under reduced pressure and purified by silica gel column chromatography (dichloromethane:methanol=95:5) to give the compound (11). To a solution of the obtained compound (11) and N-hydroxysuccinimide (58 mg) in THF (2 ml) was added dicyclohexylcarbodiimide (36 mg), and then stirred for 1.5 days at room temperature. The residue was filtered off, the filtrate was concentrated under reduced pressure. The residue was purified by silica gel column chromatography (hexane:ethyl acetate=2:8) to give the compound (12) (15 mg) having the following physical data.

TLC: Rf 0.41 (ethyl acetate); NMR (CDCl$_3$): δ4.70–4.25 (2H, m), 4.19 (2H, t), 3.02–2.92 (2H, m), 2.87 (4H, s), 2.8–2.73 (2H, m), 2.63 (1H, d), 1.90–1.60 (6H, m); MS: m/z 372, 277, 185, 93, 75.

(b) Succinimide 3-(4-hydroxy-2-oxotetrahydropyran-4-yl-)propyl octadienoate (1) To a suspension of 63% sodium hydride (657 mg) in DMF (20 ml) was added separately several time adipic acid (3.00 g) at room temperature. The mixture was stirred for 30 min. To the mixture was added slowly dropwise benzylbromide (2.00 ml). The mixture was stirred for 1.5 days at 80° C. The reaction mixture was diluted with 1N hydrochloric acid, and then was extracted with ethyl acetate. The residue was purified by silica gel column chromatography (hexane:ethyl acetate=1:1) to give the compound (14) (1.68 g) having the following physical data.

TLC: Rf 0.53 (hexane:ethyl acetate=4:6).

(2) A solution of the compound (14) (200 mg) in thionyl chloride (2 ml) was refluxed for 2 hours, and then the mixture was concentrated under reduced pressure. To a solution of the residue in THF (1 ml) was added slowly dropwise a mixture of a solution of the compound (10) (100 mg) and pyridine (300 µl) in THF (1.0 ml) at room temperature, and then the mixture was stirred for 1.5 hours. The reaction mixture was diluted with water, and extracted with ethyl acetate. The residue was purified by silica gel column chromatography (hexane:ethyl acetate=1:1) to give the compound (16) (160 mg) having the following physical data.

TLC: Rf 0.16 (hexane:ethyl acetate=6:4).

(3) To a solution of the compound (16) (160 mg) in methanol (4 ml) was added 10% palladium-carbon (50 mg). The mixture was stirred for 1.5 hours at room temperature under an atmosphere of hydrogen. The catalyst was filtered off and the filtrate was evaporated to give the compound (17). To a solution of thus obtained compound and N-hydroxysuccinimide (46 mg) in DMF (2 ml) was added dicyclohexylcarbodiimide (76 mg) and the mixture was stirred for 18 hours at room temperature. The reaction mixture was filtered off, the filtrate was diluted with water, extracted with ethyl acetate, and concentrated under reduced pressure. The residue was purified by silica gel column chromatography (hexane:ethyl acetate=1:4) to give the compound (18) (87 mg) having the following physical data.

TLC: Rf 0.55 (ethyl acetate); NMR (CDCl$_3$): δ4.70–4.27 (2H, m), 4.20 (2H, t), 2.85 (4H, s), 2.70–2.45 (4H, m), 2.33 (2H, t), 1.95–1.55 (8H, m), 1.55–1.23 (4H, m).

(c) 3-(4-hydroxy-2-oxotetrahydropyran-4-yl)propyl iodoacetate (1) To a solution of the compound (10) (24 mg) and iodoacetic anhydride (65 mg) in THF (1.0 ml) was added 4-dimethylaminopyridine (26 mg) at room temperature, and then the mixture was stirred for 1 hours. The reaction mixture was diluted with water, extracted with ethyl acetate, and concentrated under reduced pressure. The residue was purified by silica gel column chromatography (hexane:ethyl acetate=1:2) to give the compound (19) (22 mg) having the following physical data.

TLC: Rf 0.57 (ethyl acetate); NMR (CDCl$_3$): δ4.70–4.30 (2H, m), 4.21 (2H, t), 3.72 (2H, s), 2.68 (1H, d), 2.53 (1H, d), 1.97–1.63 (6H, m).

(d) Succinimide 11-(4-hydroxy-2-oxotetrahydropyran-4-yl) undecanoate (1) To a solution of the compound (25) [prepared by the same procedure described hereinbefore from (a)-(1) to (a)-(5) by using 1,1 2-dodecandiol as starting material] (3.00 g) in methanol (20 ml) was added 10% palladium-carbon (550 mg). The mixture was stirred for 1.5 hours at room temperature under an atmosphere of hydrogen. The catalyst was filtered off and the filtrate was concentrated under reduced pressure to give the compound (26) (2.20 g) having the following physical data.

TLC: Rf 0.13 (hexane:ethyl acetate=7:3).

(2) To a solution of the compound (26) (2.20 g) in acetone (30 ml) was dropped Jones reagent (7.0 ml) at 4° C. After the reaction mixture was stirred for 10 min., isopropanol (2.0 ml) was added thereto. After stirred for 10 min., the reaction mixture was extracted with ethyl acetate, and concentrated under reduced pressure. A solution of thus obtained product in methanol (20 ml) was treated with diazomethane, and concentrated under reduced pressure. The residue was purified by silica gel column chromatography (hexane:ethyl acetate=9:1) to give the compound (28) (2.04 g) having the following physical data.

TLC: Rf 0.33 (hexane:ethyl acetate=7:3).

(3) To a solution of diisopropylamine (2.67 ml) in diethylether (13 ml) was added slowly dropwise 1.56M n-butyllithium in hexane solution (10.8 ml) at −20° C., and then the mixture was stirred for 1 hour. Ethyl acetate (1.69 ml) was added slowly dropwise thereto at −78° C., and then the mixture was stirred for 30 min. A solution of the compound (28) (1.826 g) in diethylether (15 ml) was added thereto. The reaction mixture was stirred for 30 min. The reaction mixture was diluted with a saturated aqueous solution of ammonium chloride, and extracted with ethyl acetate. The residue was purified by silica gel column chromatography (hexane:ethyl acetate=9:1) to give the compound (29) (1.785 g) having the following physical data.

TLC: Rf 0.47 (hexane:ethyl acetate=7:3).

(4) To a solution of the compound (29) (311 mg) in methanol (20 ml) was added 1N aqueous solution of sodium hydroxide (2.9 ml). The mixture was stirred for four hours at room temperature and quenched by addition of 1N hydrochloric acid, and then extracted with ethyl acetate to give the compound (30) (221 mg) having the following physical data.

TLC: Rf 0.72 (hexane:ethyl acetate=99:1).

(5) To a solution of the compound (30) (220 mg) and N-hydroxysuccinimide (126 mg) in THF (5 ml) were added dicyclohexylcarbodiimide (326 mg) and the mixture was stirred for 1.5 days at room temperature. The reaction mixture was filtered off, the filtrate was concentrated under reduced pressure. The residue was purified by silica gel column chromatography (hexane:ethyl acetate=1:1) to give the compound (31) (210 mg) having the following physical data.

TLC: Rf 0.24 (hexane:ethyl acetate=4:6); NMR (CDCl$_3$): δ4.68–4.28 (2H, m), 2.83 (4H, s), 2.70–2.45 (4H, m), 2.0–1.2 (14H, m); MS: m/z 283, 265, 247, 237, 223, 169, 115, 98.

(e) Succinimide 5-(4-hydroxy-2-oxotetrahydropyran-4-yl)pentanoate (1) To a solution of the compound (8) (320 mg) in methanol (10 ml) was added 10% palladium-carbon (150 mg). The mixture was stirred for 3 hours at room temperature under an atmosphere of hydrogen. The catalyst was filtered off and the filtrate was concentrated under reduced pressure to give the compound (32) (290 mg) having the following physical data.

TLC: Rf 0.12 (hexane:ethyl acetate=1:1).

(2) To a solution of oxalyl chloride (27 μl) in dichloromethane (1 ml) was added dropwise a solution of DMSO (45 μl) in dichloromethane (0.5 ml) at −78° C., and then the mixture was stirred for 10 min. A solution of the compound (32) (50 mg) in dichloromethane (1.0 ml) was added thereto, and then the mixture was stirred for 40 min. Triethylamine (145 μl) was added thereto. The reaction mixture was warm to −30° C. for the period of 30 min. The mixture was diluted with water, and extracted with ethyl acetate. The crude product was purified by silica gel column chromatography (hexane:ethyl acetate=2:1) to give the compound (33) (28 mg) having the following physical data.

TLC: Rf 0.38 (hexane:ethyl acetate=1:1).

(3) To a solution of the compound (33) (50 mg) in THF (2 ml) was added methyl (triphenylphosphoranylidene)acetate (76 mg) and the mixture was stirred for 2.5 days at room temperature. The reaction mixture was concentrated under reduced pressure. The residue was purified by silica gel column chromatography (hexane:ethyl acetate=3:1) to give the compound (34) (54 mg) having the following physical data.

TLC: Rf 0.53 (hexane:ethyl acetate=1:1).

(4) To a solution of the compound (34) (54 mg) in methanol (2 ml) was added 5% palladium-carbon (50 mg). The mixture was stirred for 30 min. at room temperature under an atmosphere of hydrogen. The catalyst was filtered off and the filtrate was concentrated under reduced pressure to give the compound (35) (48 mg) having the following physical data.

TLC: Rf 0.53 (hexane:ethyl acetate=1:1).

(5) To a solution of the compound (35) (48 mg) in methanol (1.5 ml) was added 1N aqueous solution of sodium hydroxide (600 μl) at room temperature. The reaction mixture was stirred for 4.5 hours. The mixture was neutralized by addition of 1N hydrochloric acid (600 μl), and then concentrated under reduced pressure. The residue was purified by silica gel column chromatography (ethyl acetate:methanol=95:5) to give the compound (38) (35 mg) having the following physical data.

TLC: Rf 0.10 (ethyl acetate:methanol=8:2).

(6) To a solution of the compound (38) (20 mg) in THF (1.0 ml) was added successively N-hydroxysuccinimide (16 mg) and dicyclohexylcarbodiimide (29 mg), and the mixture was stirred for 22 hours at room temperature. The reaction mixture was filtered off, the filtrate was concentrated under reduced pressure. The residue was purified by silica gel column chromatography (hexane:ethyl acetate=3:7) to give the compound (39) (11 mg) having the following physical data.

TLC: Rf 0.31 (ethyl acetate); NMR (CDCl$_3$): δ4.70–4.30 (2H, m), 2.85 (4H, s), 2.75–2.48 (4H, m), 1.95– 1.73 (4H, m), 1.73–1.45 (4H, m); MS: m/z 199, 181, 163, 139, 115, 98, 85.

(f) Succinimide 4-(4-hydroxy-4-methyl-2-oxotetrahydropyran-6-yl)benzoate (1) To a solution of methyl 4-formylbenzoate (40) (1.36 g) in a mixture of acetone (4.4 ml) and DME (8.2 ml) was added vigorously stirring 0.03N aqueous solution of sodium hydroxide (13.35 ml) under cooling with ice. The mixture was stirred for 45 min., and added 1N hydrochloric acid (700 μl). The reaction mixture was extracted with ethyl acetate, and purified by silica gel column chromatography (hexane:ethyl acetate=7:3) to give the compound (41) (1.252 g) having following physical data.

TLC: Rf 0.58 (hexane:ethyl acetate=4:6).

(2) To a solution of the compound (41) (1.252 g) in acetic anhydride (1.0 ml) was added triethylamine (1.56 ml) at room temperature, and the mixture was stirred for 30 min. at same temperature. The reaction mixture was quenched by addition of 1N hydrochloric acid (20 ml). The reaction mixture was extracted with ethyl acetate, and purified by silica gel column chromatography (hexane:ethyl acetate=8:2) to give the compound (42) (682 mg) having following physical data.

TLC: Rf 0.61 (hexane:ethyl acetate=4:6).

(3) To a solution of diisopropylamine (742 μl) in diethylether (5 ml) was added slowly dropwise 1.56M n-butyllithium in hexane solution (2.89 ml) at −20° C., and then the mixture was stirred for 1 hour. Ethyl acetate (452 μl) was added slowly dropwise thereto at −78° C., and then the mixture was stirred for 30 min. A solution of the compound (42) (582 mg) in THF (5 ml) was added thereto. The reaction mixture was stirred for 30 min. The mixture was diluted with a saturated aqueous solution of ammonium chloride, and extracted with ethyl acetate. The residue was purified by silica gel column chromatography (hexane:ethyl acetate= 7:3) to give the compound (43) (703 mg) having the following physical data.

TLC: Rf 0.37 (hexane:ethyl acetate=6:4).

(4) To a solution of the compound (43) (110 mg) in methanol (4 ml) was added 1N aqueous solution of sodium hydroxide (1.14 ml) under cooling with ice. The mixture was stirred for 20 hours at room temperature. The reaction mixture was: neutralized by addition of 1N hydrochloric acid, and then extracted with ethyl acetate. The residue was purified by silica gel column chromatography (ethyl acetate:methanol:acetic acid=8:2:0.1) to give the compound (44) (73 mg) having the following physical data.

TLC: Rf 0.36 (ethyl acetate:acetic acid=98:2).

(5) To a solution of the compound (44) (59 mg) in THF (4 ml) was added successively N-hydroxysuccinimide (54 mg) and dicyclohexylcarbodiimide (97 mg), and the mixture was stirred for 20 hours at room temperature. The reaction mixture was filtered off, the filtrate was concentrated under reduced pressure. The residue was purified by silica gel column chromatography (hexane:ethyl acetate=3:7) to give the compound (45) (60 mg) having the following physical data.

TLC: Rf 0.67 (ethyl acetate); NMR (CDCl$_3$): δ8.15 (2H, d), 7.55 (2H, d), 5.83–5.3 (1H, m), 3.0–2.55 (6H, m), 2.35–1.4 (5H, m).

(g) Succinimide 4-((4-hydroxy-2-oxotetrahydropyran-4-yl)carbonylamino) phenylacetate (1) To a solution of p-nitrophenylacetic acid (46) (1.84 g) in DMF (17 ml) was added successively ethyl iodide (1.5 ml) and potassium carbonate (2.0 g). The mixture was stirred for 6 hours at 70° C. The reaction mixture was extracted with ethyl acetate, and the extract was concentrated under reduced pressure. The residue was purified by silica gel column chromatography (hexane:ethyl acetate=9:1) to give the compound (47) (3.22 g) having the following physical data.

TLC: Rf 0.43 (hexane:ethyl acetate=8:2).

(2) To a solution of the compound (47) (3.32 g) in methanol (15 ml) was added 10% palladium-carbon (700 mg). The mixture was stirred for 3 hours at room temperature under an atmosphere of hydrogen. The catalyst was filtered off and the filtrate was concentrated under reduced pressure. The obtained residue was added successively 2-hydroxy-γ-butyrolactone (4.24 g) and dimethylaminopyridine (388 mg), and the mixture was stirred for 3 hours at 90° C. The reaction mixture was purified by silica gel column chromatography (hexane:ethyl acetate=8:2) to give the compound (48) (2.49 g) having the following physical data.

TLC: Rf 0.38 (ethyl acetate).

(3) To a solution of the compound (48) (2.49 g) in dichloromethane (25 ml) was added successively pyridine (3.58 ml) and slowly dropwise acetyl chloride (0.78 ml) under cooling with ice, and the mixture was stirred for 1 hour. The reaction mixture was diluted with water, and extracted with ethyl acetate, and purified by silica gel column chromatography (hexane:ethyl acetate=6:4) to give the compound (49) (1.74 g) having following physical data.

TLC: Rf 0.44 (hexane:ethyl acetate=4:6).

(4) To a solution of the compound (49) (1.74 g) in acetone (25 ml) was added Jones reagent (5 ml) at 4° C. After the reaction mixture was stirred for 20 min., isopropanol (2 ml) was added thereto. The reaction mixture was extracted with ethyl acetate and purified by silica gel column chromatography (hexane:ethyl acetate=7:3) to give the compound (50) (447 mg) having the following physical data.

TLC: Rf 0.80 (hexane:ethyl acetate=4:6).

(5) To a solution of diisopropylamine (109 μl) in diethylether (1 ml) was added slowly dropwise 1.56M n-butyllithium in hexane solution (0.40 ml) at −20° C., and then the mixture was stirred for 1 hour. Ethyl acetate (62 μl) was added slowly dropwise thereto at −78° C., and then the mixture was stirred for 30 min. A solution of the compound (50) (50 mg) in THF (0.60 ml) was added thereto. The mixture was stirred for 30 min. The reaction mixture was diluted with a saturated aqueous solution of ammonium chloride, and extracted with ethyl acetate. The residue was purified by silica gel column chromatography (hexane:ethyl acetate=6:4) to give the compound (51) (50 mg) having the following physical data.

TLC: Rf 0.17 (hexane:ethyl acetate=6:4).

(6) To a solution of the compound (51) (39 mg) in methanol (1 ml) was added 1N aqueous solution of sodium hydroxide (0.38 ml) under cooling with ice. The mixture was stirred for 3 hours at room temperature. The reaction mixture was neutralized by addition of 1N hydrochloric acid, and then extracted with ethyl acetate to give the compound (52) (25 mg) having the following physical data.

TLC: Rf 0.72 (ethyl acetate:methanol:acetic acid= 80:15:5).

(7) To a solution of the compound (52) (25 mg) in THF (1 ml) was added successively N-hydroxysuccinimide (20 mg) and dicyclohexylcarbodiimide (35 mg), and the mixture was stirred for 18 hours at room temperature. The reaction mixture was filtered off, the filtrate was concentrated under reduced pressure. The residue was purified by silica gel column chromatography (hexane:ethyl acetate=3:7) to give the compound (53) (19 mg) having the following physical data.

TLC: Rf 0.58 (ethyl acetate); NMR (d6-acetone): δ7.78 (2H, d), 7.38 (2H, d), 4.6–4.3 (2H, m), 4.02 (2H, s), 3.65–3.58 (1H, m), 3.2–2.0 (8H, m).

(h) Succinimide 3-(4-hydroxy-4-methyl-2-oxotetrahydropyran-6-yl) propionate (1) To a solution of the compound (3) (5.4 g) in acetone (180 ml) was added vigorously stirring 1.44M sodium ethoxide (3.1 ml) under cooling with ice, and the mixture was stirred for 15 sec., and quenched by addition of 1N hydrochloric acid (7.5 ml). The reaction mixture was extracted with ethyl acetate, and purified by silica gel column chromatography (hexane:ethyl acetate=65:35) to give the compound (54) (2.942 g) having the following physical data.

TLC: Rf 0.31 (hexane:ethyl acetate=6:4).

(2) To a solution of the compound (54) (2.942 g) in dichloromethane (60 ml) was added camphorsulfonic acid (12 mg). Dihydropyran (2.27 ml) was added slowly dropwise thereto at 0° C. The mixture was stirred for 2 hour at room temperature, and then triethylamine (0.1 ml) was added thereto. The reaction mixture was extracted with ethyl acetate, and purified by silica gel column chromatography (hexane:ethyl acetate=9:1) to give the compound (55) (4.0 g).

To a solution of diisopropylamine (6.03 ml) in diethylether (60 ml) was added slowly dropwise 1.56M n-butyllithium in hexane solution (22.4 ml) at −20° C., and then the mixture was stirred for 1.5 hours. Ethyl acetate (3.49 ml) was added slowly dropwise there to at −78° C., and then the mixture was stirred for 55 min. A solution of the compound (55) (4 g) in diethylether (10 ml) was added thereto. The mixture was stirred for 40 min. The reaction mixture was diluted with a saturated aqueous solution of ammonium chloride, and extracted with ethyl acetate. The residue was purified by silica gel column chromatography (hexane:ethyl acetate=7:3) to give the compound (56) (5.0 g) having the following physical data.

TLC: Rf 0.56 (hexane:ethyl acetate=6:4).

(3) To a solution of the compound (56) (1.517 g) in methanol (6 ml) was added 0.55N aqueous solution of sodium hydroxide (13.7 ml) under cooling with ice. The mixture was stirred for 4 hours at room temperature. The reaction mixture was neutralized by addition of 1N hydrochloric acid (5 ml), and then extracted with ethyl acetate, and concentrated under reduced pressure. To a solution of the obtained residue in methanol (55 ml) was added 10% palladium-carbon (600 mg). The mixture was stirred for 1 hour at room temperature under an atmosphere of hydrogen. The catalyst was filtered off and the filtrate was concentrated under reduced pressure to give the compound (57) (0.50 g) having the following physical data.

TLC: Rf 0.08 (ethyl acetate).

(4) To a solution of the compound (57) (240 mg) in acetone (24 ml) was added Jones reagent (0.7 ml) at 4° C. After the mixture was stirred for 15 min., isopropanol (2 ml) was added thereto, and the mixture was stirred for 5 min. The reaction mixture was diluted with chloroform, and added anhydrous magnesium sulfate, and filtered through Celite. The filtrate was concentrated under reduced pressure, and purified by silica gel column chromatography (methanol:ethyl acetate=1:9) to give the compound (58) (188 mg) having the following physical data.

TLC: Rf 0.67 (ethyl acetate:methanol:acetic acid= 80:15:5).

(5) To a solution of the compound (58) (171 mg) in THF (2 ml) was added successively N-hydroxysuccinimide (194 mg) and dicyclohexylcarbodiimide (279 mg), and the mixture was stirred for 60 hours at room temperature. The reaction mixture was filtered off, the filtrate was concentrated under reduced pressure. The residue was purified by silica gel column chromatography (hexane:ethyl acetate= 2:8) to give the compound (59) (154 mg) having the following physical data.

TLC: Rf 0.36 (ethyl acetate); NMR (CDCl$_3$): δ4.9–4.35 (1H, m), 2.9–2.4 (6H, m), 2.16–1.46 (6H, m), 1.4 (3H, m); MS: m/z 281 (M$^+$-18), 185, 157, 129, 97.

Example 2: Preparation of antigens for immunization

To a solution of a conjugate of a mevalonic acid derivative prepared in Example 1 and a spacer (compound (12), 18 μmol) in methanol (71 μl) was added 0.5M phosphate buffer (abbreviated as PB hereinafter, pH 7.4, 71 μl), and the mixture was stirred for 10 min. 50 mM PB (pH 7.4, 3.8 ml) containing bovine serum albumin (abbreviated as BSA hereinafter, 60 mg) was added thereto, and the mixture was stirred for 6 hours at room temperature. The reaction mixture was dialyzed with 10 mM PB at 4° C. to give the desired antigen for immunization (BSA-(12)).

To a solution of the compound (12) (27 μmol) in methanol (105 pl) was added PBS (pH 7.4, 105 μl), and the mixture was stirred for 10 min. PBS (pH 7.4, 6.4 ml) containing keyhole limpet hemocyanin (abbreviated as KLH hereinafter, 86 mg (purity is 69%)) was added thereto, and the mixture was stirred for 6 hours at room temperature. The reaction mixture was dialyzed with PBS (pH 7.4) at 4° C. to give the desired antigen for immunization (KLH-(12)).

The desired antigens for immunization, BSA-(18), KLH-(18), BSA-(19), KLH-(19), BSA-(31), KLH-(31), BSA-(39), KLH-(39), BSA-(45), KLH-(45), BSA-(53), KLH-(53), BSA-(59) and KLH-(59) were given by the same procedure as above.

Example 3: Preparation of rabbit polyclonal antibody

An emulsion of PBS (500 μl) containing each of various antigens for immunization prepared in Example 2 (1 mg as BSA when a BSA-conjugate is used, or 1 mg as KLH when a KLH-conjugate is used), and FCA (500 μl) was subcutaneously administered to a male New Zealand White Rabbit aged seven weeks. After about 4 weeks, the rabbit was sensitized four times for each 2 weeks, by an emulsion of a PBS solution (500 μl) containing of the antigen for immunization prepared by the same procedure as hereinbefore described, and FICA (500 μl).

After the first, third and fifth immunization by the antigen for immunization and FICA, the titer of antibody in blood was measured by the method shown below.

Blood was collected from the rabbit and to the serum prepared (50 μl) were added successively water (450 μl), 0.5% γ-globulin (80 μl) and a saturated aqueous solution of ammonium sulfate (580 μl), and then the mixture was centrifuged. The precipitation was dissolved into 50 mM PB (200 μl), and 50 mM PB (100 μl) containing R-[2-$^{14}$C] mevalonic acid (400 Bq) was added thereto and the mixture was reacted overnight at 4° C. To the mixture was added successively 0.1M PB (200 μl) containing 0.5% bovine γ-globulin and 30% polyethylene glycol 6000 (register trademark, Wako Pure Chem. Ind. Ltd., 600 μl), and then the mixture was centrifuged. Radioactivity of the precipitation was measured. After the third immunization, the sufficiently high titer of antibody in blood serum using KLH-(12) as antigen for immunization was obtained. This blood serum was called as polyclonal antibody, KLH-(12)R.

The desired polyclonal antibodies, BSA-(18)R, KLH-(18)R, BSA-(19)R, KLH-(19)R, BSA-(31)R, KLH-(31)R, BSA-(39)R, KLH-(39)R, BSA-(45)R, KLH-(45)R, BSA-(53)R, KLH-(53)R, +BSA-(59)R and KLH-(59)R were given by the same procedure as described above.

Example 4: Preparation of mouse polyclonal antibody

An emulsion of PBS (100 µl) containing each of various antigens for immunization prepared in Example 2 (120 µg as BSA when a BSA-conjugate is used or 120 µg as KLH when a KLH-conjugate is used), and FCA (100 µl) was intraperitoneally administered to a male BALB/c mouse aged eight weeks. After about 2 weeks, the mouse was immunized five times every 2 weeks, by an emulsion of a PBS solution (100 µl) containing of the antigen for immunization and FICA (100 µl), prepared by the same procedure as hereinbefore described After the second and fifth immunization With the antigen for immunization and FICA, the titer of antibody in blood was measured by the method shown below.

50 mM PB containing a conjugate of a mevalonic acid derivative and a carrier-protein (being different from a conjugate used as an antigen for immunization) was placed with 100 µl portions in a polystyrene 96 wells micro plate (prepared by NUNC Co.). The micro plate was allowed to stand for 1.5 hours at room temperature to be fixed. After the removal of an aqueous layer, 50 mM PB (400 µl) containing 0.5% BSA (when KLH is used as a carrier-protein of an antigen for immunization) or ovalbumin (abbreviated as OVA hereinafter, when BSA is used as a carrier-protein of an antigen for immunization) (abbreviated as BSA(OVA)-PB hereinafter), was added to block the inside of a wall of wells for 1 hour at room temperature.

After the removal of an aqueous layer, 50 mM PB (100 µl) containing or not containing mevalonic acid (100 µg) was added. A dilute solution of the serum obtained from the mouse (diluted with 0.1% BSA(OVA)-PB 1000 to 100000 times) was added thereto with 100 µl portions and then the mixture was reacted for 1 hour at room temperature. After the removal of an aqueous layer, the dishes were washed twice with 50 mM PB (300 pl) containing 0.05% TWEEN 20 (polyoxyethylene(20) sorbitan monolaurate). Anti-mouse IgG antibody labeled with peroxidase (prepared by Vector Co.), which is diluted with 0.1% BSA-(OVA)PB 10000 times, was added thereto with 100 µl portions and then the mixture was reacted for 1 hour at room temperature. After the removal of an aqueous layer, the dishes were washed twice with 50 mM PB containing 0.05% TWEEN 20 (polyoxyethylene(20) sorbitan monolaurate). A substrate solution (a mixture of dimethylsulfoxide, water, 0.1M citric acid containing 20 mM 3,3',5,5'-tetramethylbenzidine, McIlvaine buffer solution (pH 4.57) and 14 mM an aqueous solution of hydrogen peroxide at the proportion of 4:46:2:38:10, 250 µl) was added thereto and then the mixture was reacted for 15 minutes at room temperature. After the reaction was stopped by the addition of 1N sulfuric acid (50 µl), and the absorbance was measured at 450 nm. The serums which were sufficiently recognized the difference between the absobance in the presence of mevalonic acid and that in the absence, were called as polyclonal antibodies, KLH-(12)M, KLH-(18)M, BSA-(19)M, KLH-(31)M, KLH-(39)M, KLH-(45)M, KLH-(53)M and KLH-(59)M based on antigens for immunization thereof, respectively.

Example 5: Preparation of mouse monoclonal antibody (1) Immunization of mouse

Immunization of mice was carried out by the same procedure as example 4 under the condition as below:

(i) Method for Immunization antigen for immunization: KLH-(39) the number of immunization by FICA: 10 times (ii) Method for the measurement of the titer of antibody antigen using to be fixed: BSA-(12) (50 mM PB containing 100 ng, 10 ng or 1 ng of BSA (100 µl))

After the tenth immunization by FICA, it was confirmed that the titer of antibody rose sufficiently. And after two weeks, PBS (100 µl) containing an antigen for immunization (300 µg as KLH) was intraperitoneally administrated.

(2) Cell fusion

After three days from the intraperitoneal administration of PBS containing the antigen for immunization, the spleen was taken out from the immunized mouse prepared in Example 5. The spleen cells thus obtained were mixed with mouse myeloma cells, SP-2/0-Ag14 (prepared by the method described in Nature, 276, 269 (1978)) at the proportion of 5:1, and polyethylene glycol (PEG 4000 (for gas chromatography), prepared by E. Merck) was added thereto at a concentration of 50%. The cell fusion was carried out according to the Goding method (J. Immunol. Methods, 39, 285 (1980)).

A mixture of cells after cell fusion was suspended into Dulbecco's modified Eagle medium (abbreviated as DME hereinafter) (containing 4.5 g/l glucose, prepared by GIBCO Co.) containing 20% fetal bovine serum (FBS), 10% NCTC 109 medium (registered trademark, prepared by MA Bio-product Co.), hypoxanthine (13.6 pg/ml), thymidine (3.9 µg/ml) and glycine (2.0 µg/ml), and cultured under an atmosphere containing 5% $CO_2$, at 37° C. The culture was continued by replacing a half quantity of a medium by HAT medium (the above Eagle medium containing 0.18 µg/ml of aminopterin), at the 2nd, 4th and 7th day after the culture. After about ten days from the culture, colonies like bunches of grapes were formed in some wells, and finally the multiplication of hybridoma was confirmed in 801 wells.

Screening of cells producing monoclonal antibody was carried out by the method shown below.

(3) Screening of cells producing monoclonal antibody 50 mM PB containing BSA-(12) (1 ng as BSA) was placed with 100 µl portions in a polystyrene 96 wells micro plate (prepared by NUNC Co.). The micro plate was allowed to stand for 1.5 hours at room temperature to be fixed. After the removal of an aqueous layer, 50 mM PB (400 µl) containing 0.5% BSA was added to block the inside of a wall of wells for 1 hour at room temperature.

After the removal of an aqueous layer, 50 mM PB (100 µl) containing or not containing mevalonic acid (100 µg) was added. A dilute solution of incubation supernatant of hybridomas (diluted with 50 mM PB containing 0.1% BSA 50 times) was added thereto with 100 µl portions and then the mixture was reacted for 1 hour at room temperature. After the removal of an aqueous layer, the dishes were washed twice with 50 mM PB (300 µl) containing 0.05% TWEEN 20 (polyoxyethylene(20) sorbitan monolaurate). Anti-mouse IgG antibody labeled with peroxidase (prepared by Vector Co.), which is diluted with 50 mM PB containing 0.1% BSA 10000 times, was added thereto with 100 µl portions and then the mixture was reacted for 1 hour at room temperature. After the removal of an aqueous layer, the dishes were washed twice with 50 mM PB containing 0.05% TWEEN 20 (polyoxyethylene(20) sorbitan monolaurate). A substrate solution (prepared in example 4, 250 µl) was added thereto and then the mixture was reacted for 15 minutes at room temperature. After the reaction was stopped by the addition of 1N sulfuric acid (50 µl), and the absorbance was measured at 450 nm. The wells, whose incubation supernatants were sufficiently recognized the difference between the absorbance in the presence of mevalonic acid and that in the absence, were judged that they contained the hybridomas producing a monoclonal antibody for mevalonic acid.

(4) Culture of hybridomas producing an antibody

Cloning of the cells, which were judged to produce an antibody for mevalonic acid, was carried out by the soft agar culture method according to the kennett method (Monoclonal Antibodies, 372 (1980)). The cloned cells were named MHM-9H.

The cloned cells ($10^7$ piece) were intraperitoneally administered to a female BALB/c mouse previously treated with pristane. After about two weeks, when much ascites fluid were stored, and they were collected. The antibody in the collected ascites fluid was collected with an aqueous solution of ammonium sulfate at 50% saturation and purified by affinity column chromatography using protein A-cephalos CL 4B column (prepared by Pharmacia Co.), and IgG fraction was obtained.

The hybridoma producing MHM-9H, a monoclonal antibody of the present invention, was deposited in National Institute of Bioscience and Human-Technology as deposited number FERM BP-4524 at Jan. 6, 1994.

(5) Immunoglobulin subclass of monoclonal antibody

On the monoclonal antibody, MHM-9H, screening of its subclass was carried out by using mouse mono Ab-ID EIA kit (prepared by Zymed Co.). As the result, it was proved MHM-9H was mouse $IgG_{2b}$, κ.

Example 6: Cross-reaction of rabbit polyclonal antibody with various analogues of mevalonic acid To 50 mM PB containing 400 Bq of R-[2-$^{14}$C] mevalonic acid (100 µl) was added successively a solution of antibody (the mixture of the polyclonal antibody KLH-(12)R of the present invention, water, 0.5% γ-globulin and a saturated aqueous solution of ammonium sulfate in the ratio of 0.5:4.5:0.8 5.8 was centrifugalized, and the obtained precipitation was dissolved into a solution of 50 mM PB of four times as much as amount of the used polyclonal antibody, 100 µl) and a standard solution of mevalonic acid analogous compound as indicated following table (a solution of 50 mM PB, 100 µl) in the polystyrene tube, and then the mixture was allowed to stand overnight at 4° C. To the reaction mixture was added a solution of 0.5% γ-globulin (200 µl), and further added 30% polyethylene glycol 6000 (600 µl), and then the mixture was centrifuged. The precipitation was dissolved into 0.1N aqueous solution of sodium hydroxide, and added the liquid of scintillator (1 ml), and measured radioactivity. The result was indicated in table 1.

TABLE 1

| Analogues of mevalonic acid | $IC_{50}$ (µg/test) | cross-reactivity (%) |
|---|---|---|
| Mevalonic acid | 0.065 | 100 |
| Glutaric acid* | >6500 | <0.001 |
| 3-Methylglutaric acid* | 1000 | 0.0065 |
| 3-Hydroxy-3-methylglutaric acid | 500 | 0.013 |

*There is possibility that glutaric acid and derivatives thereof are much in the sample.

It was understood that an antibody of the present invention bound specifically to mevalonic acid of low-concentration, and cross-reactivity with the other mevalonic acid analogues was very low as below 0.1%.

Example 7: Cross-reaction of mouse monoclonal antibody with various analogues of mevalonic acid.

A solution of antibody (prepared in example 10 as hereinafter defined) was placed with 100 µl portions in a polystyrene 96 wells micro plate (prepared by NUNC Co.). The micro plate was allowed to stand for 1.5 hours at room temperature to be fixed. After the removal of an aqueous layer, 50 mM PB (400 µl) containing 0.5% BSA was added to block the inside of a wall of wells for 1 hour at room temperature.

After the removal of an aqueous layer, 50 mM PB (100 µl) containing mevalonic acid analogues of various concentrations was added. A solution of labeled antigen (prepared in example 10 as hereinafter defined) was added thereto with 100 µl portions and then the mixture was allowed to stand overnight at 4° C. After the removal of an aqueous layer, the dishes were washed twice with 50 mM PB (300 µl) containing 0.05% TWEEN 20 (polyoxyethylene(20) sorbitan monolaurate). The substrate solution (prepared in example 9 as hereinafter, 250 µl) was added thereto and then the mixture was reacted for 15 minutes at room temperature. After the reaction was stopped by the addition of 1N sulfuric acid (50 µl), and the absorbance was measured at 450 nm. The result was indicated in table 2.

TABLE 2

| Analogues of mevalonic acid | $IC_{50}$ (µg/test) | cross-reactivity (%) |
|---|---|---|
| Mevalonic acid | 0.0025 | 100 |
| Glutaric acid | >250 | <0.001 |
| 3-Methylglutaric acid | >250 | <0.001 |
| 3Hydroxy-3-methylglutaric acid | >250 | <0.001 |

It was understood that an monoclonal antibody of the present invention bound specifically to mevalonic acid of low-concentration, and cross-reaction of the other mevalonic acid analogues compound was very low as below 0.001%.

Example 8: immunoassay of mevalonic acid by using rabbit polyclonal antibody (Radioimmunoassay)

(1) Preparation of immunoassay reagent of mevalonic acid (a) A solution of antibody The mixture of the polyclonal antibody KLH-(12)R, water, 0.5% γ-globulin and a saturated aqueous solution of ammonium sulfate in the ratio of 0.5:4.5:0.8:5.8 was centrifuged, and the obtained precipitation was dissolved into a solution of 50 mM PB of four times as much as amount of the used polyclonal antibody, KLH-(12)R.

(b) A solution of labeled antigen 50 mM PB containing 400 Bq of R-[2-$^{14}$C] mevalonic acid.

(c) A standard solution

Mevalonic acid was prepared to become 10000 µg/ml, 100 µg/ml, 10 µg/ml, 1 µg/ml, 0.1 µg/ml and 0.01 µg/ml with 50 mM PB.

(2) Assay of mevalonic acid by using reagent prepared in (1)

To a solution of antibody (100 µl) was added successively a solution of labeled antigen (100 µl) and a solution of standard (or sample) (100 µl) in the polystyrene tube, and then the mixture was allowed to stand overnight at 4° C. To the reaction mixture was added successively a solution of 0.5% γ-globulin (200 µl) and 30% polyethylene glycol 6000 (600 µl), and then was centrifuged. The precipitation was dissolved into 0.1N aqueous solution of sodium hydroxide, and added the liquid of scintillator (1 ml), and measured radioactivity. FIG. 1 indicated standard calibration curves, which was made by plotting $B/B_0$ calculated from measured radioactivity. It was obvious from FIG. 1 that the assay system of the present invention is possible to measure of the quantity of mevalonic acid in the range of 20 to 1000 ng/test.

Example 9: immunoassay of mevalonic acid by using mouse polyclonal antibody (Enzyme immunoassay, solid phase antigen method)

(1) Preparation of immunoassay reagent (a) A solution of the second antibody (B or O)

Anti-mouse IgG antibody labeled with the horse-radish peroxidase (prepared by Vector Co.), which was diluted with 50 mM PB containing 0.1 BSA 10000 times (a solution of the second antibody (B)), and which was diluted with 50mM PB containing 0.1% OVA 10000 times (a solution of the second antibody (O)).

(b) A solution of the first antibody

Polyclonal antibody shown in table 3 of the present invention was diluted with 50 mM PB containing 0.1% BSA or OVA to the magnification in table 3. (It was diluted with PB containing BSA in case of antibody which was obtained by using KLH as antigens for immunization, and it was diluted with PB containing OVA in case of antibody which was obtained by using BSA.)

(c) A solution of antigen

A conjugate of a mevalonic acid derivative and a carrier-protein was prepared to become the concentration shown in table 3 with 50 mM PB.

(d) A standard solution

Mevalonic acid was prepared to become 1 mg/ml and 100 µg/ml, 10 µg/ml, 1 µg/ml, 100ng/ml and 10 ng/ml with 50 mM PB.

(e) A washing solution 50 mM PB containing 0.05 TWEEN 20 (polyoxyethylene(20) sorbitan monolaurate)

(f) A blocking solution 50 mM PB containing 0.5% BSA (Blocking solution (B))
50 mM PB containing 0.5% OVA (Blocking solution (O))

(g) A substrate solution

Dimethylsulfoxide, distilled water, 0.1M citric acid containing 20 mM 3,3',5,5'-tetramethylbenzidine, McIlvaine buffer and 14 mM aqueous solution of hydrogen peroxide in the ratio of 4:46:2:38:10 was mixed.

(h) A stopping solution 1N sulfuric acid (2) Assay of mevalonic acid by using reagent prepared in (1).

A solution of antigen was placed with 100 µl portions in a polystyrene 96 wells micro plate (prepared by NUNC Co.). The micro plate was allowed to stand for 1.5 hours at room temperature to be fixed. After the removal of an aqueous layer, a solution of blocking (B) or (O) was added to block the inside of a wall of wells for 1 hour at room temperature.

After the removal of an aqueous layer, a standard solution (100 µl) was added thereto. A solution of the first antibody was added thereto with 100 µl portions and then the mixture was reacted for 1 hour at room temperature. After the removal of an aqueous layer, the dishes were washed twice with a washing solution (300 µl). A solution of the second antibody (B) or the second antibody (O) was added thereto with 100 µl portions and then the mixture was reacted for 1 hour at room temperature. After the removal of an aqueous layer, the dishes were washed twice with a washing solution. A substrate solution (250 µl) was added thereto and then the mixture was reacted for 15 minutes at room temperature. After a stopping solution (50 µl) added thereto, and the absorbance was measured at 450 nm.

On all mouse polyclonal antibody, standard calibration curves were made by plotting $B/B_0$ calculated from the measured absorbance.

A condition of measurement and a range of calibration of each polyclonal antibody were indicated in table 3, and a standard calibration curve of polyclonal antibody, KLH-(39)M, was indicated in FIG. 2.

TABLE 3

| Polyclonal antibody | The dilution rate of the first antibody | The coated and the concentration (µg/ml) | A solution of the second antibody and blocking | $IC_{50}$ (µg/test) | The range of calibration (µg/test) |
| --- | --- | --- | --- | --- | --- |
| KLH-(12)M | $10^4$ | BSA-(31) 0.01 | (B) | 0.5 | 0.07–7 |
| KLH-(18)M | $2 \times 10^3$ | BSA-(31) 0.01 | (B) | 0.3 | 0.06–3 |
| BSA-(19)M | $2 \times 10^3$ | KLH-(31) 0.01 | (O) | 3.6 | 0.3–30 |
| KLH-(31)M | $10^5$ | BSA-(12) 0.01 | (B) | 0.7 | 0.2–8 |
| KLH-(39)M | $3 \times 10^4$ | BSA-(12) 0.01 | (B) | 0.1 | 0.02–2 |
| KLH-(45)M | $2 \times 10^3$ | BSA-(12) 0.1 | (B) | 4.0 | 0.6–20 |
| KLH-(53)M | $5 \times 10^2$ | BSA-(39) 1 | (B) | 6.0 | 1–30 |

Example 10: Immunoassay of mevalonic acid by using mouse monoclonal antibody (Enzyme immunoassay, solid phase of the first antibody method)

(1) Preparation of immunoassay reagent (a) A solution of enzyme-labeled antigen

A conjugate (18) of mevalonic acid derivative and a specer (prepared in example 1(b), 175 nmol) was added to PBS (175 μl) containing a horseradish peroxidase (prepared by Toyobo, 350 μg) and then the mixture was reacted for 2 hours at room temperature and then overnight at 4° C. The reaction mixture was dialyzed by a mixture of 1,4-dioxane and PBS (1:1) and then by PBS. An obtained enzyme-labeled antigen was diluted with 50 mM PB containing 0.1% BSA to become 1.25 ng/100 μl (as peroxidase protein).

(b) A solution of antibody

Monoclonal antibody of the present invention, MHM-9H (prepared in example 5), was prepared by 50 mM PB to become 7 μg/ml.

(c) A standard solution

Mevalonic acid was prepared by 50 mM PB to become 500 ng/ml, 200 ng/ml, 80ng/ml, 32 ng/ml, 12.8 ng/ml, 5.12 ng/ml, 2.04 ng/ml and 0.82 ng/ml.

(d) A washing solution 50 mM PB containing 0.05% TWEEN 20 (polyoxyethylene(20) sorbitan monolaurate)

(e) A blocking solution 50 mM PB containing 0.5% BSA (f) A substrate solution

Dimethylsulfoxide, distilled water, 0.1M citric acid containing 20 mM 3,3',5,5'-tetrabenzidine, McIlvaine buffer (pH 4.57) and 14 mM aqueous solution of hydrogen peroxide in the ratio of 4:46:2:38:10 was mixed.

(g) A stopping solution 1N sulfuric acid (2) Assay of mevalonic acid by using reagent prepared in (1).

1) A solution of antibody (prepared by method as the above mentioned) was placed with 100 μl portions in a polystyrene 96 wells micro plate. The micro plate was allowed to stand for 1.5 hours at room temperature. After the removal of an aqueous layer, a blocking solution (400 μl) was added thereto and the mixture was allowed to stand for 1 hour at room temperature.

3) After the removal of an aqueous layer, a standard solution or sample (100 μl) was added thereto and then a solution of labeled antigen (100 μl) was added thereto and the mixture was allowed to stand overnight at 4° C.

4) After the removal to an aqueous layer, the dishes were washed twice with a washing solution.

5) A substrate solution (250 μl) was added thereto and then the mixture was reacted for 15 minutes at room temperature.

6) A stopping solution (50 μl) was added thereto.

7) The absorbance was measured at 450 nm.

FIG. 3 indicated standard calibration curves, which was made by plotting $B/B_0$ calculated from the measured absorbance. It was obvious from FIG. 3 that the assay system of the present invention is possible to measure the amount of mevalonic acid in the range of 0.4–20 ng/test.

Example 11: Immunoassay of mevalonic acid in human urine

Normal human urine and normal human urine added mevalonic acid of a known quantity (each 2 ml) were pretreated with the reverse phase Sep-PakPS-1 column (prepared by Waters Co.), and the fraction containing mevalonic acid was obtained. Assay of mevalonic acid in this fraction was carried out by immunoassay indicated in example 10. The result was indicated in table 4.

TABLE 4

| (a) Linearity test | |
|---|---|
| urine (μl/test) | measured value of mevalonic acid (ng/ml urine) |
| 1    18 | 221 |
| 2    39 | 231 |

| (b) Recovery test | | | |
|---|---|---|---|
| before addition of mevalonic acid (ng/ml) | added mevalonic acid (ng/ml) | measured value after addition (ng/ml) | recovery (%) |
| 1   226 | 563 | 791 | 100.4 |
| 2   226 | 563 | 784 | 99.1 |

From the linearity test, the amount of the mevalonic acid in normal human urine which we measured was much the same as that reported in several papers. Though the amount of urine used by measurement was changed, the measured value was agreed with each other. Therefor the result of linearity test was good. Moreover, the result of recovery test was good.

It was indicated from the above that immunoassay of present invention for mevalonic acid was very easy and practical measurement method.

BRIEF DESCRIPTION OF FIGURE

FIG. 1 was indicated calibration curves in immunoassay system of mevalonic acid by using polyclonal antibody, KLH-(12)R of the present invention.

FIG. 2 was indicated calibration curves in immunoassay system of mevalonic acid by using polyclonal antibody, KLH-(39)M of the present invention.

FIG. 3 was indicated calibration curves in immunoassay system of mevalonic acid by using monoclonal antibody, MHM-9H of the present invention.

Figure 1:
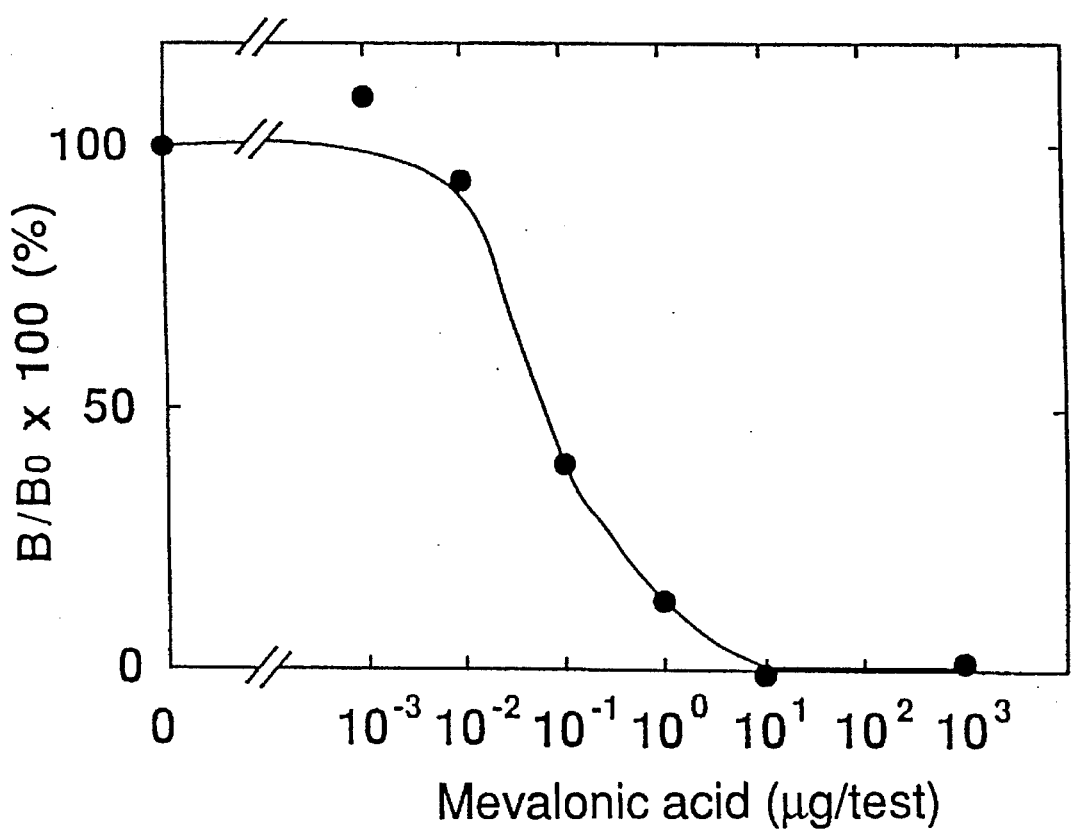
FIG. 1
Figure 2:
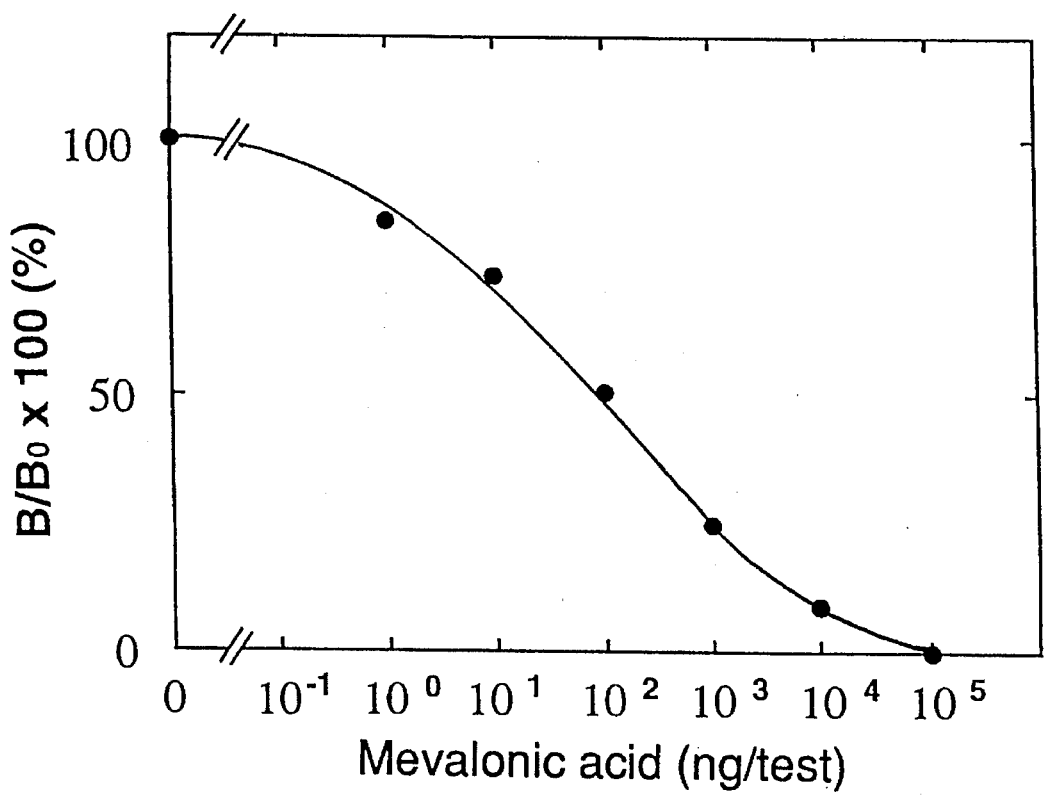
FIG. 2
Figure 3:
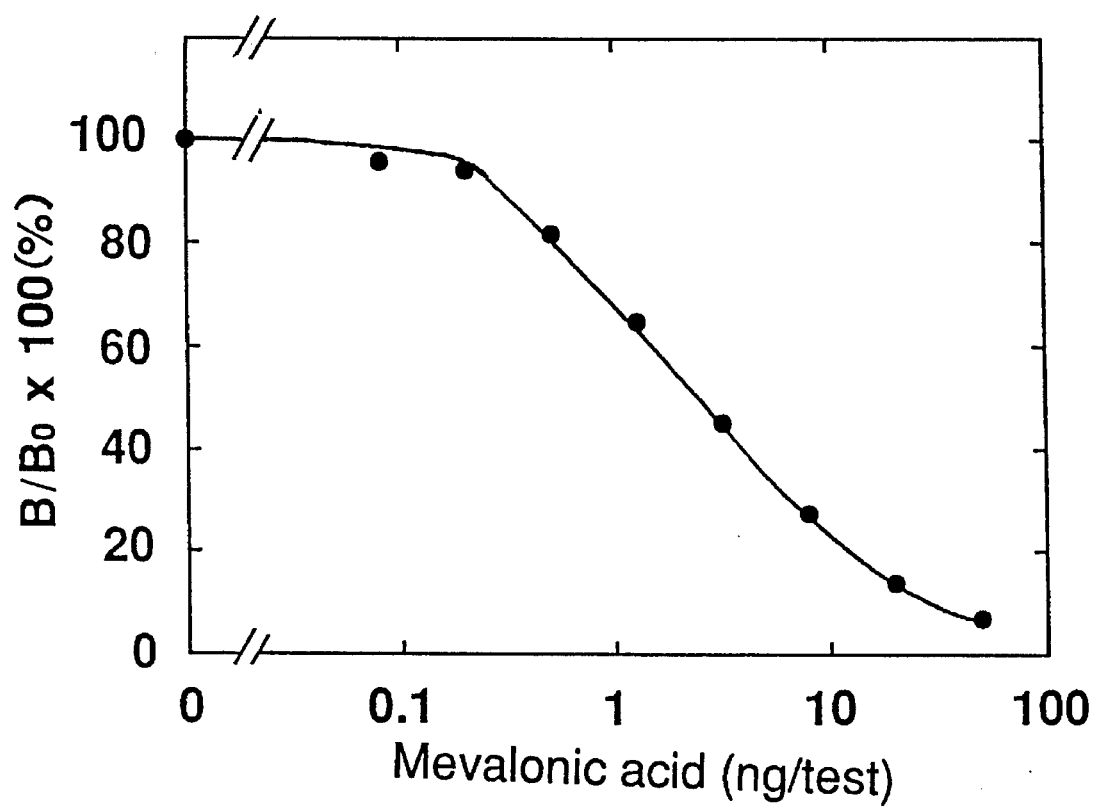
FIG. 3

What is claimed is:

1. An antibody specifically binds to mevalonic acid which is obtained by using, as antigen, a conjugate of protein selected from the group consisting of albumin, globulin, thyroglobulin, hemocyanin, edestin, and polylysine and a mevalonic acid derivative selected from the group consisting of the formula:

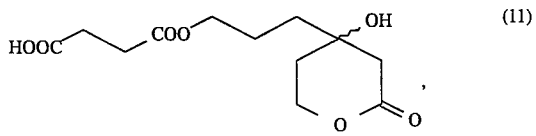

(11)

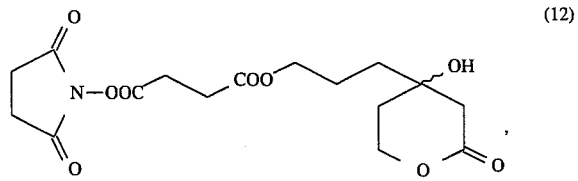

(12)

-continued

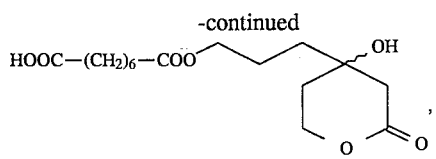

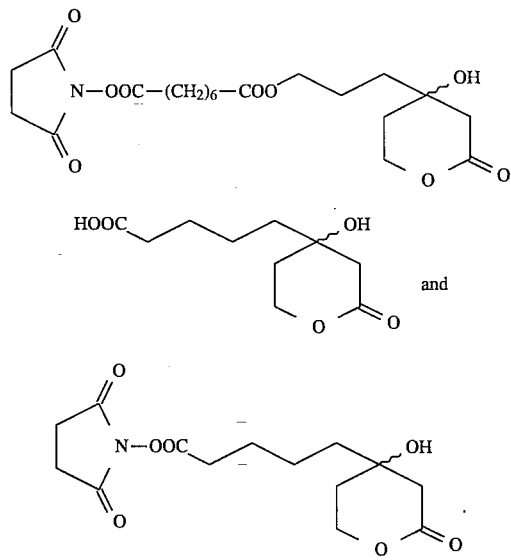

2. An antibody according to claim 1, which is a polyclonal antibody.

3. An antibody according to claim 2, which is a rabbit polyclonal antibody.

4. An antibody according to claim 2, which a polyclonal antibody obtained by using as an antigen, a conjugate of keyhole limpet hemocyanin (KLH) and succinimide 3-(4-hydroxy-2-oxotetrahydropyran-4-yl)propyl succinate of the formula:

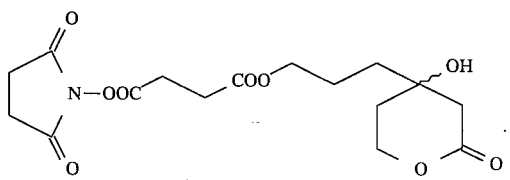

5. An antibody according to claim 1, which is mouse polyclonal antibody.

6. An antibody according to claim 2, which is polyclonal antibody obtained by using as an antigen, a conjugate of keyhole limpet hemocyanin (KLH) and succinimide 5-(4-hydroxy-2-oxotetrahydropyran-4-yl)pentanoate of the formula:

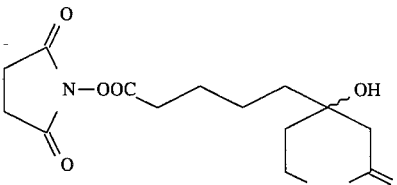

7. An antibody according to claim 1, which is a monoclonal antibody.

8. An antibody according to claim 7, which is mouse monoclonal antibody.

9. An antibody according to claim 7, which is monoclonal antibody obtained by using as an antigen, a conjugate of keyhole limpet hemocyanin (KLH) and succinimide 5-(4-hydroxy-2-oxotetrahydropyran-4-yl)pentanoate of the formula:

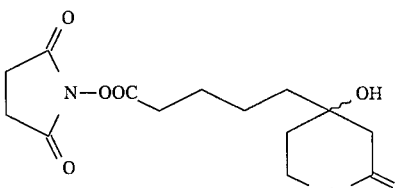

10. An antibody of claim 7, which is monoclonal antibody, MHM-9H, produced by hybridoma cell line deposited as FERM BP-4524.

* * * * *